(12) United States Patent
Fox et al.

(10) Patent No.: US 10,751,059 B2
(45) Date of Patent: Aug. 25, 2020

(54) CIRCULAR STAPLING INSTRUMENT ANVIL WITH SHANK HAVING UNITARY LATCHES WITH LIVING HINGE

(71) Applicant: ETHICON LLC, Guaynabo, PR (US)

(72) Inventors: William D. Fox, New Richmond, OH (US); Gregory J. Bakos, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 218 days.

(21) Appl. No.: 15/717,301

(22) Filed: Sep. 27, 2017

(65) Prior Publication Data

US 2019/0090875 A1     Mar. 28, 2019

(51) Int. Cl.
*A61B 17/115* (2006.01)
*A61B 17/00* (2006.01)
*B23B 35/00* (2006.01)
*B21D 41/02* (2006.01)
*A61B 90/00* (2016.01)

(52) U.S. Cl.
CPC . *A61B 17/1155* (2013.01); *A61B 2017/00367* (2013.01); *A61B 2017/00473* (2013.01); *A61B 2017/00477* (2013.01); *A61B 2017/00526* (2013.01); *A61B 2090/0811* (2016.02); *B21D 41/028* (2013.01); *B23B 35/00* (2013.01)

(58) Field of Classification Search
CPC ...... A61B 17/1155; A61B 2017/00367; A61B 2090/0811; A61B 2017/00526
USPC ............................................ 227/175.1–182.1
See application file for complete search history.

(56) References Cited

U.S. PATENT DOCUMENTS

| | | | |
|---|---|---|---|
| 4,752,024 A | 6/1988 | Green et al. | |
| 5,205,459 A | 4/1993 | Brinkerhoff et al. | |
| 5,271,544 A | 12/1993 | Fox et al. | |
| 5,275,322 A | 1/1994 | Brinkerhoff et al. | |
| 5,285,945 A * | 2/1994 | Brinkerhoff | A61B 17/115 227/179.1 |
| 5,292,053 A | 3/1994 | Bilotti et al. | |

(Continued)

FOREIGN PATENT DOCUMENTS

| | | | |
|---|---|---|---|
| EP | 3 108 825 A2 | 12/2016 | |
| EP | 3 108 828 A2 | 12/2016 | |

OTHER PUBLICATIONS

European Search Report, Extended, and Written Opinion dated Feb. 12, 2019 for Application No. EP 18196906.4, 12 pgs.

(Continued)

*Primary Examiner* — Robert F Long
*Assistant Examiner* — Xavier A Madison
(74) *Attorney, Agent, or Firm* — Frost Brown Todd LLC

(57) ABSTRACT

An apparatus includes a body, an end effector, a trocar, and an anvil. The anvil head includes an annular surface defining a plurality of staple forming pockets. The plurality of staple forming pockets are configured to deform the plurality of staples when the anvil is in the staple forming position. The shank extends proximally from the annular stapling head. The shank and the anvil head cooperatively define a bore dimensioned to receive a portion of the trocar. The shank defines a lateral opening. The latch member is pivotally coupled with the shank via a living hinge. The latch member comprises a latch shelf configured to selectively couple the anvil with trocar when the trocar is inserted into the bore.

20 Claims, 19 Drawing Sheets

(56) References Cited

U.S. PATENT DOCUMENTS

| | | | |
|---|---|---|---|
| 5,333,773 | A | 8/1994 | Main et al. |
| 5,350,104 | A | 9/1994 | Main et al. |
| 5,533,661 | A | 7/1996 | Main et al. |
| 7,794,475 | B2 | 9/2010 | Hess et al. |
| 8,910,847 | B2 | 12/2014 | Nalagatla et al. |
| 9,289,207 | B2 | 3/2016 | Shelton, IV |
| 9,463,022 | B2 | 10/2016 | Swayze et al. |
| 9,498,222 | B2 | 11/2016 | Scheib et al. |
| 9,532,783 | B2 | 1/2017 | Swayze et al. |
| 9,572,573 | B2 | 2/2017 | Scheib et al. |
| 9,597,081 | B2 | 3/2017 | Swayze et al. |
| 9,724,100 | B2 | 8/2017 | Scheib et al. |
| 2005/0116009 | A1* | 6/2005 | Milliman ............ A61B 17/068 227/176.1 |
| 2011/0261666 | A1 | 10/2011 | Vlutters et al. |
| 2012/0292372 | A1 | 11/2012 | Nalagatla et al. |
| 2012/0292373 | A1 | 11/2012 | Nalagatla et al. |
| 2012/0325888 | A1* | 12/2012 | Qiao ................. A61B 17/115 227/175.1 |
| 2014/0158747 | A1 | 6/2014 | Measamer et al. |
| 2015/0083773 | A1 | 3/2015 | Measamer et al. |
| 2016/0374671 | A1 | 12/2016 | Measamer et al. |
| 2016/0374684 | A1 | 12/2016 | Dinardo et al. |

OTHER PUBLICATIONS

International Search Report and Written Opinion dated Jan. 21, 2019 for Application No. PCT/IB2018/057311, 15 pgs.

\* cited by examiner

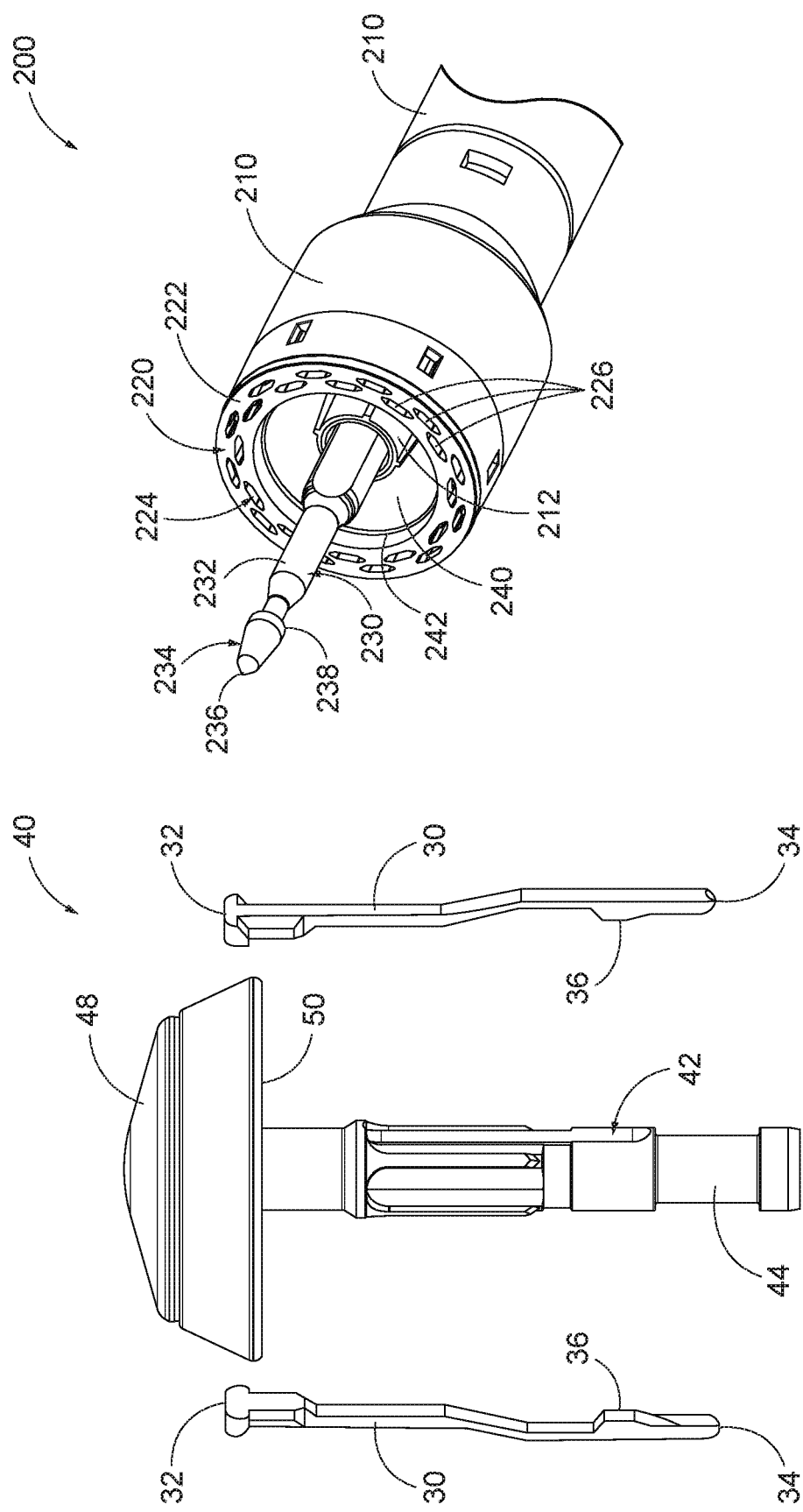

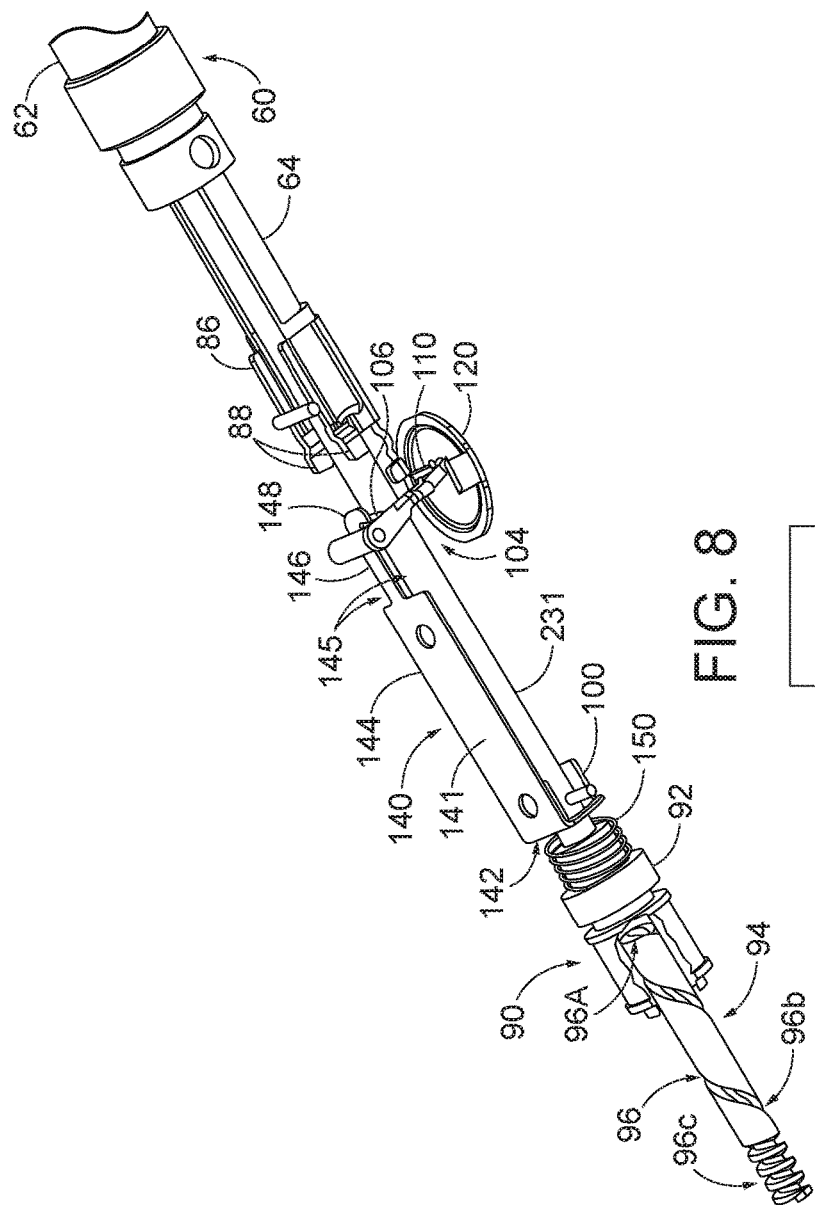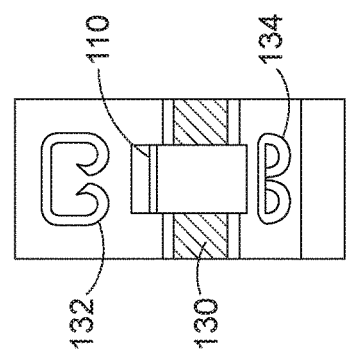

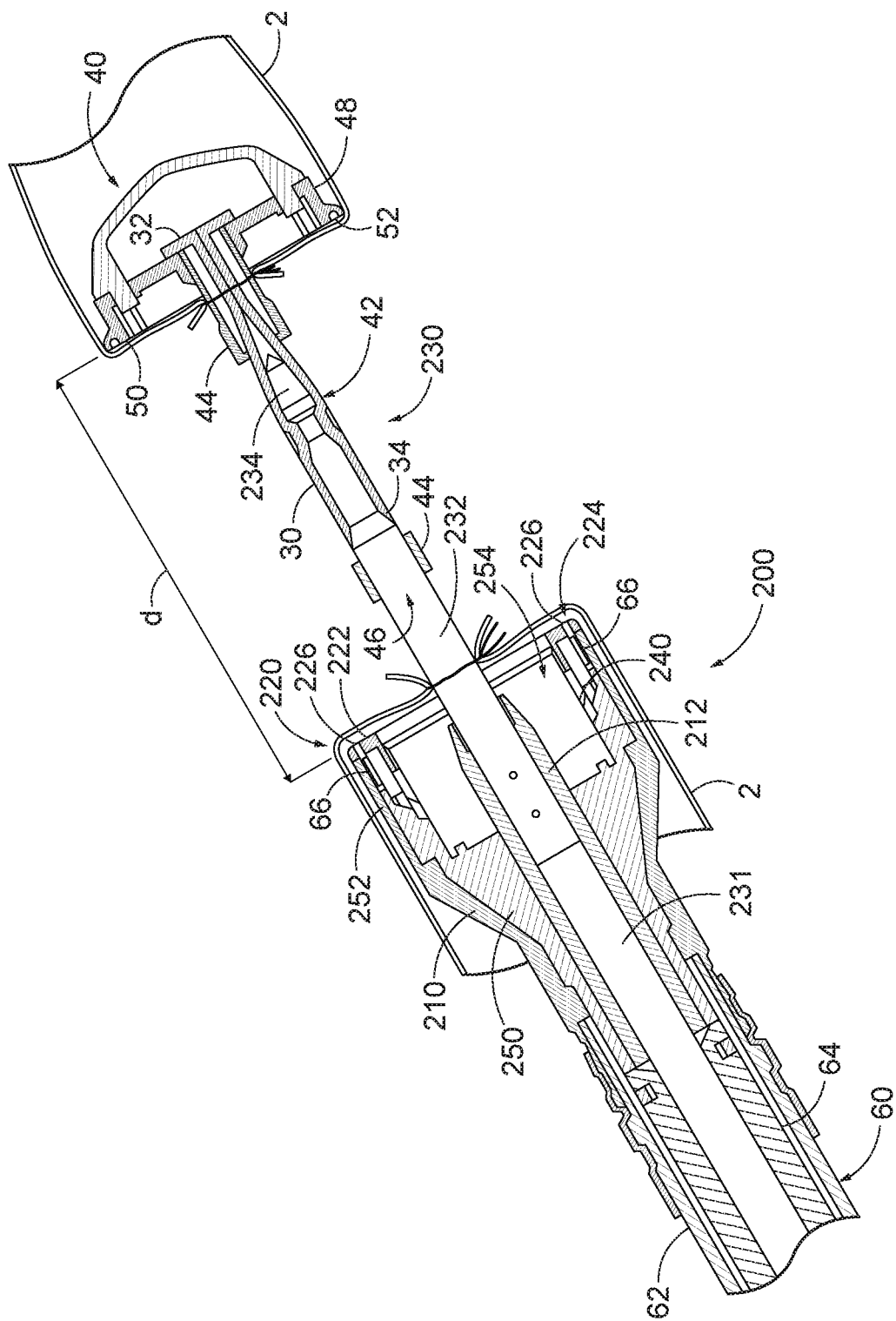

CIRCULAR STAPLING INSTRUMENT ANVIL WITH SHANK HAVING UNITARY LATCHES WITH LIVING HINGE

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. patents is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 4 depicts an exploded side elevational view of the anvil of FIG. 2;

FIG. 5 depicts a perspective view of a stapling head assembly of the surgical instrument of FIG. 1;

FIG. 8 depicts an enlarged partial perspective view of an exemplary indicator assembly of the surgical instrument of FIG. 1, showing an indicator window and indicator lever;

FIG. 9 depicts a diagrammatic view of the indicator window of FIG. 8, showing an exemplary indicator bar and exemplary corresponding staple representations;

FIG. 10A depicts an enlarged longitudinal cross-section view of the stapling head assembly of FIG. 5, showing the anvil of FIG. 2 in a first open position, where the anvil is within a first tubular portion of tissue and the stapling head assembly is within a second tubular portion of tissue;

Figure 1:
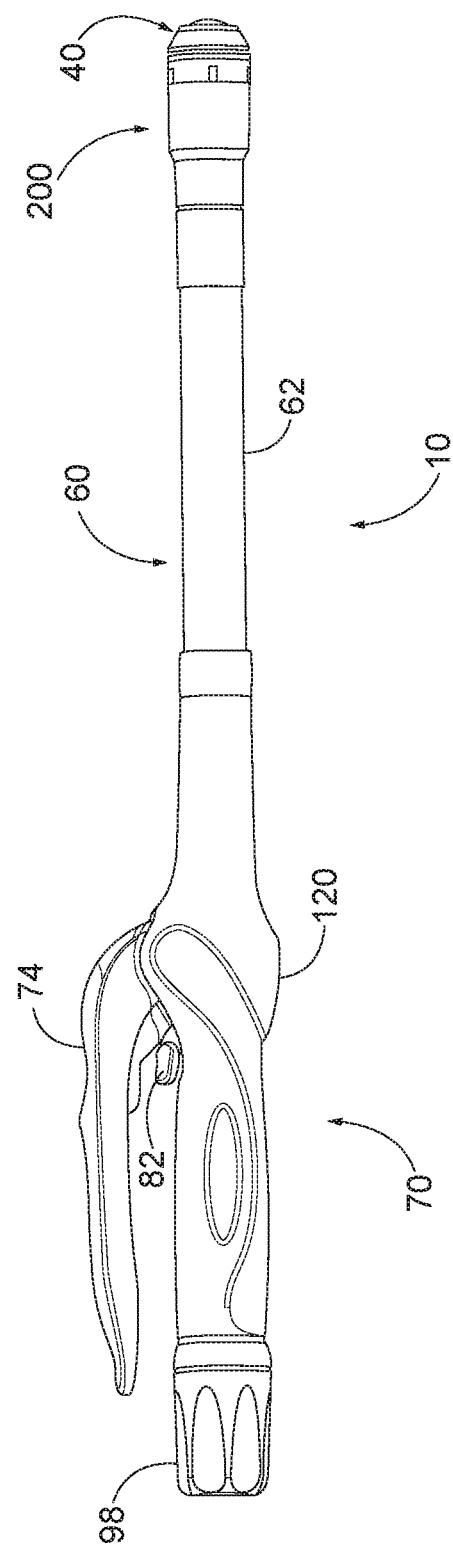
FIG. 1 depicts a side elevation view of an exemplary circular stapling surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

FIGS. 1-11 depict an exemplary circular surgical stapling instrument (10) having a stapling head assembly (200), a shaft assembly (60), and an actuator handle assembly (70), each of which will be described in more detail below. Shaft assembly (60) extends distally from actuator handle assembly (70) and stapling head assembly (200) is coupled to a distal end of shaft assembly (60). In brief, actuator handle assembly (70) is operable to actuate a staple driver member (250) of stapling head assembly (200) to drive a plurality of staples (66) out of stapling head assembly (200). Staples (66) are bent to form completed staples by an anvil (40) that is selectively attached at the distal end of instrument (10). Accordingly, tissue (2), as shown in FIGS. 10A-10E, may be stapled utilizing instrument (10).

In the present example, instrument (10) comprises a closure system and a firing system. As will be described in greater detail below, the closure system and anvil (40) are operable to clamp tissue between anvil (40) and stapling head assembly (200). As will also be described in greater detail below, the firing system and anvil (40) are operable to cut and staple tissue clamped between anvil (40) and stapling head assembly (200).

The closure system comprises a trocar (230), a trocar actuator (231), and an adjustment knob (98). Anvil (40) may be coupled to a distal end of trocar (230). Adjustment knob (98) is operable to longitudinally translate trocar (230) relative to stapling head assembly (200), thereby translating anvil (40) when anvil (40) is suitably coupled to trocar (230), and further clamping tissue between anvil (40) and stapling head assembly (200) as will be described in greater detail below.

The firing system comprises a trigger (74), a trigger actuation assembly (84), a driver actuator (64), and a staple driver member (250). Staple driver member (250) includes a knife member (240) configured to sever tissue when staple driver member (250) is actuated longitudinally. In addition, staples (66) are positioned distal to a plurality of staple drivers of staple driver member (250) such that staple driver member (250) also drives staples (66) distally when staple driver member (250) is actuated longitudinally. Thus, when trigger (74) is actuated and trigger actuation assembly (84) actuates staple driver member (250) via driver actuator (64), knife member (240) and staple drivers (252) substantially simultaneously sever tissue (2) and drive staples (66) distally relative to stapling head assembly (200) into tissue. The components and functionalities of the closure system and firing system will now be described in greater detail.

A. Exemplary Anvil

In the following discussion of anvil (40), the terms "distal" and "proximal" (and variations thereof) will be used with reference to the orientation of anvil (40) when anvil (40) is coupled with shaft assembly (60) of instrument (10). Thus, proximal features of anvil (40) will be closer to the operator of instrument (10); while distal features of anvil (40) will be further from the operator of instrument (10).

Figure 3:
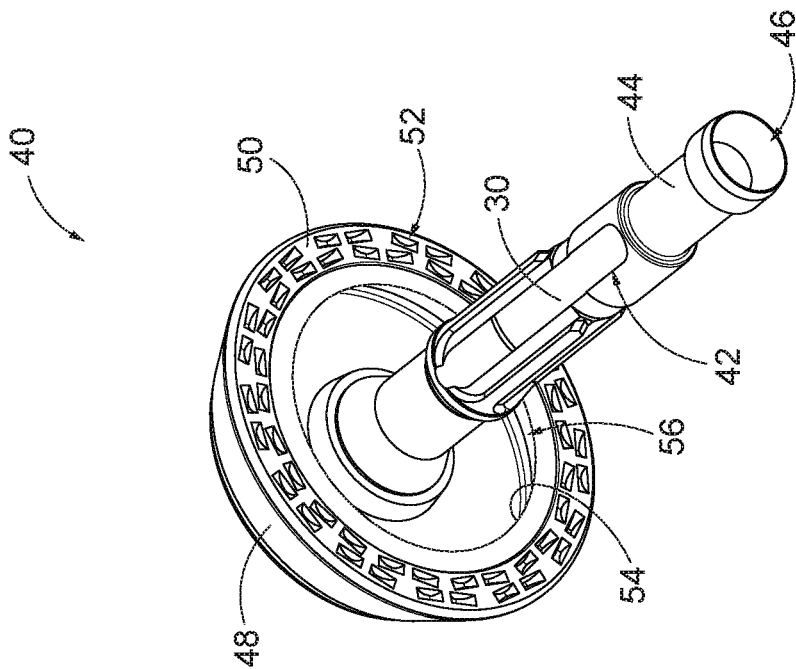
FIG. 3 depicts another perspective view of the anvil of FIG. 2.
Figure 2:
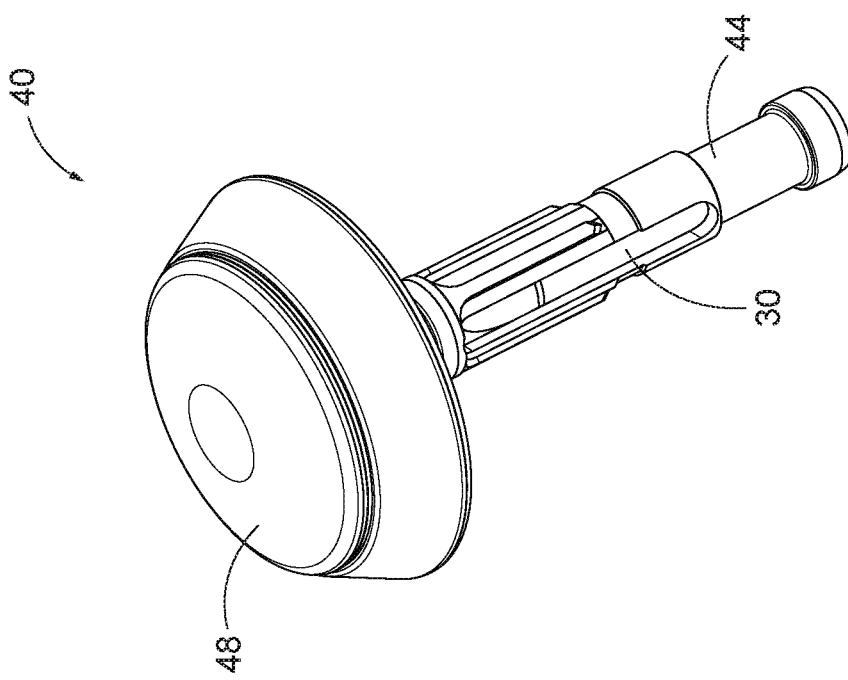
FIG. 2 depicts a perspective view of an exemplary anvil of the surgical instrument of FIG. 1.

As best seen in FIGS. 2-4, anvil (40) of the present example comprises a head (48) and a shank (44). As mentioned above and as will be described in greater detail below, anvil (40) of the present example may selectively couple to trocar (230) such that when coupled, movement of trocar (230) relative to stapling head assembly (200) also moves anvil (40) relative to stapling head assembly (200).

Head (48) includes a proximal surface (50) that defines a plurality of staple forming pockets (52). Staple forming pockets (52) are arranged in two concentric annular arrays. In some other versions, staple forming pockets (52) are arranged in three or more concentric annular arrays. Staple forming pockets (52) are configured to deform staples as the staples are driven into staple forming pockets (52). Accordingly, when anvil (40) is in the closed position and staples (66) are driven out of stapling head assembly (200) into staple forming pockets (52), each staple forming pocket (52) may deform a generally "U" shaped staple (66) into a "B" shape as is known in the art. As best seen in FIG. 4, proximal surface (50) terminates at an inner edge (54), which defines an outer boundary of an annular recess (56) surrounding shank (44).

Shank (44) defines a bore (46) and includes a pair of pivoting latch members (30) positioned in bore (46). As best seen in FIG. 4, each latch member (30) includes a "T" shaped distal end (32), a rounded proximal end (34), and a latch shelf (36) located distal to proximal end (34). "T" shaped distal ends (32) secure latch members (30) within bore (46). Latch members (30) are positioned within bore (46) such that distal ends (34) are positioned at the proximal ends of lateral openings (42), which are formed through the sidewall of shank (44). Lateral openings (42) thus provide clearance for distal ends (34) and latch shelves (36) to deflect radially outwardly from the longitudinal axis defined by shank (44). However, latch members (30) are configured to resiliently bias distal ends (34) and latch shelves (36) radially inwardly toward the longitudinal axis defined by shank (44). Latch members (30) thus act as retaining clip to allow anvil (40) to be selectively secured to trocar (230) of stapling head assembly (200). It should be understood, however, that latch members (36) are merely optional. Anvil (40) may be removably secured to a trocar (230) using any other suitable components, features, or techniques.

In addition to or in lieu of the foregoing, anvil (40) may be further constructed and operable in accordance with at least some of the teachings of U.S. Pat. Nos. 5,205,459; 5,271,544; 5,275,322; 5,285,945; 5,292,053; 5,333,773;

5,350,104; 5,533,661; 8,910,847; U.S. Pub. No, 2016/0374671, issued as U.S. Pat. No. 10,188,386 on Jan. 29, 2019; and/or U.S. Pub. No. 2016/0374684, issued as U.S. Pat. No. 10,226,253 on Mar. 12, 2019, the disclosures of which are incorporated by reference herein. Still other suitable configurations will be apparent to one of ordinary skill in the art in view of the teachings herein.

B. Exemplary Stapling Head Assembly

Figure 6:
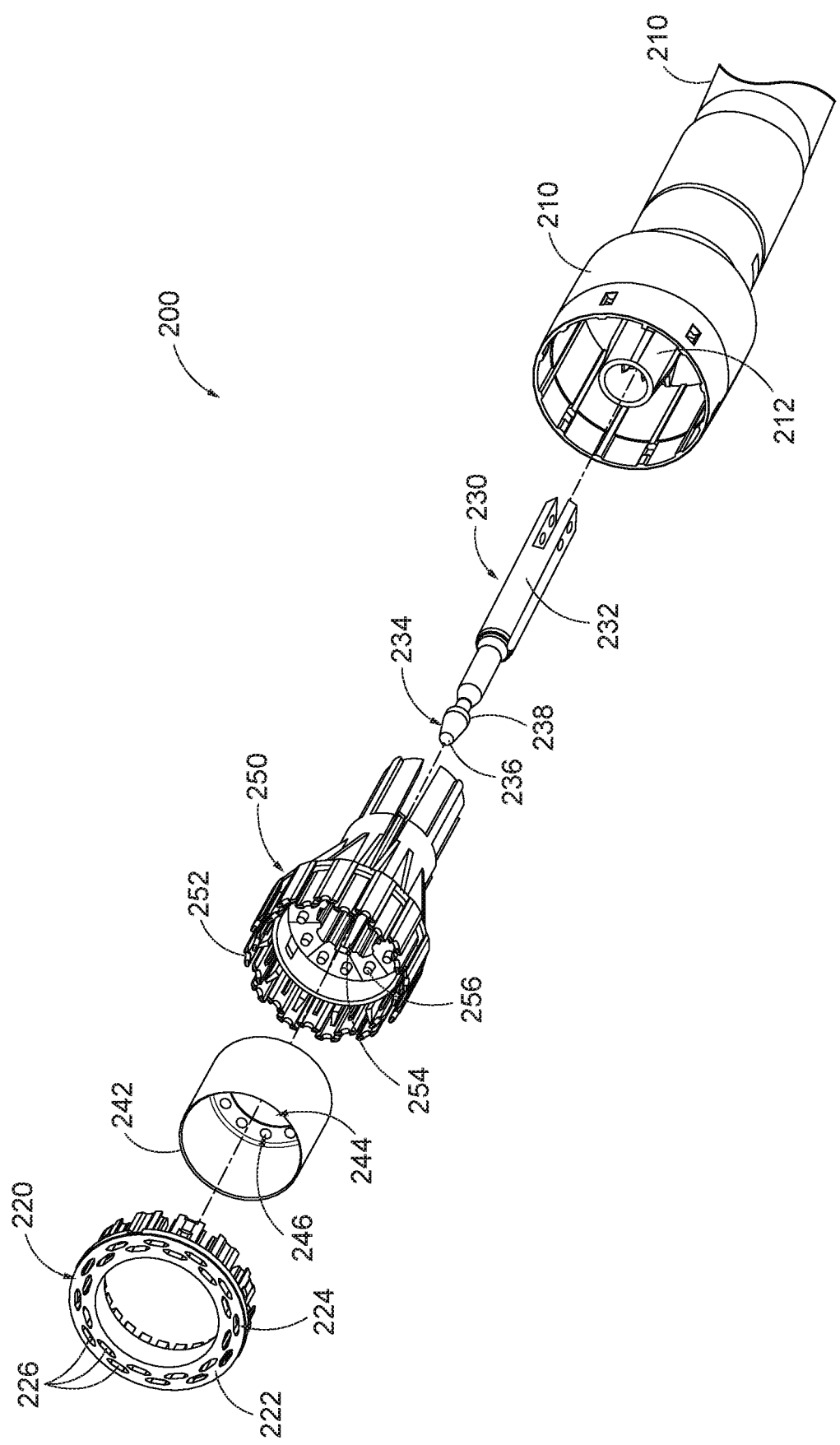
FIG. 6 depicts an exploded perspective view of the stapling head assembly of FIG. 5.

As best seen in FIGS. 5-6, stapling head assembly (200) of the present example is coupled to a distal end of shaft assembly (60) and comprises a tubular casing (210) housing a slidable staple driver member (250). A cylindraceous inner core member extends distally within tubular casing (210). Tubular casing (210) is fixedly secured to an outer sheath (62) of shaft assembly (60), such that tubular casing (210) serves as a mechanical ground for stapling head assembly (200).

Trocar (230) is positioned coaxially within inner core member (212) of tubular casing (210). As mentioned above and as will be described in greater detail below, trocar (230) is operable to translate distally and proximally relative to tubular casing (210) in response to rotation of adjustment knob (98) relative to casing (110) of handle assembly (100). Trocar (230) comprises a shaft (232) and a head (234). Head (234) includes a pointed tip (236) and an inwardly extending proximal surface (238). Shaft (232) thus provides a reduced outer diameter just proximal to head (234), with surface (238) providing a transition between that reduced outer diameter of shaft (232) and the outer diameter of head (234). While tip (236) is pointed in the present example, tip (236) is not sharp. Tip (236) will thus not easily cause trauma to tissue due to inadvertent contact with tissue. Head (234) and the distal portion of shaft (232) are configured for insertion in bore (46) of anvil (40). Proximal surface (238) and latch shelves (36) have complementary positions and configurations such that latch shelves (36) engage proximal surface (238) when shank (44) of anvil (40) is fully seated on trocar (230). Anvil (40) may thus secure to trocar (230) through a snap fitting between latch members (30) and head (234). In addition, or in the alternative, trocar (230) may include a magnetic portion (not shown) which may attract anvil (40) towards trocar (230). Still further configurations and arrangements for anvil (40) and trocar (230) will be apparent to one of ordinary skill in the art in view of the teachings herein.

Figure 10B:
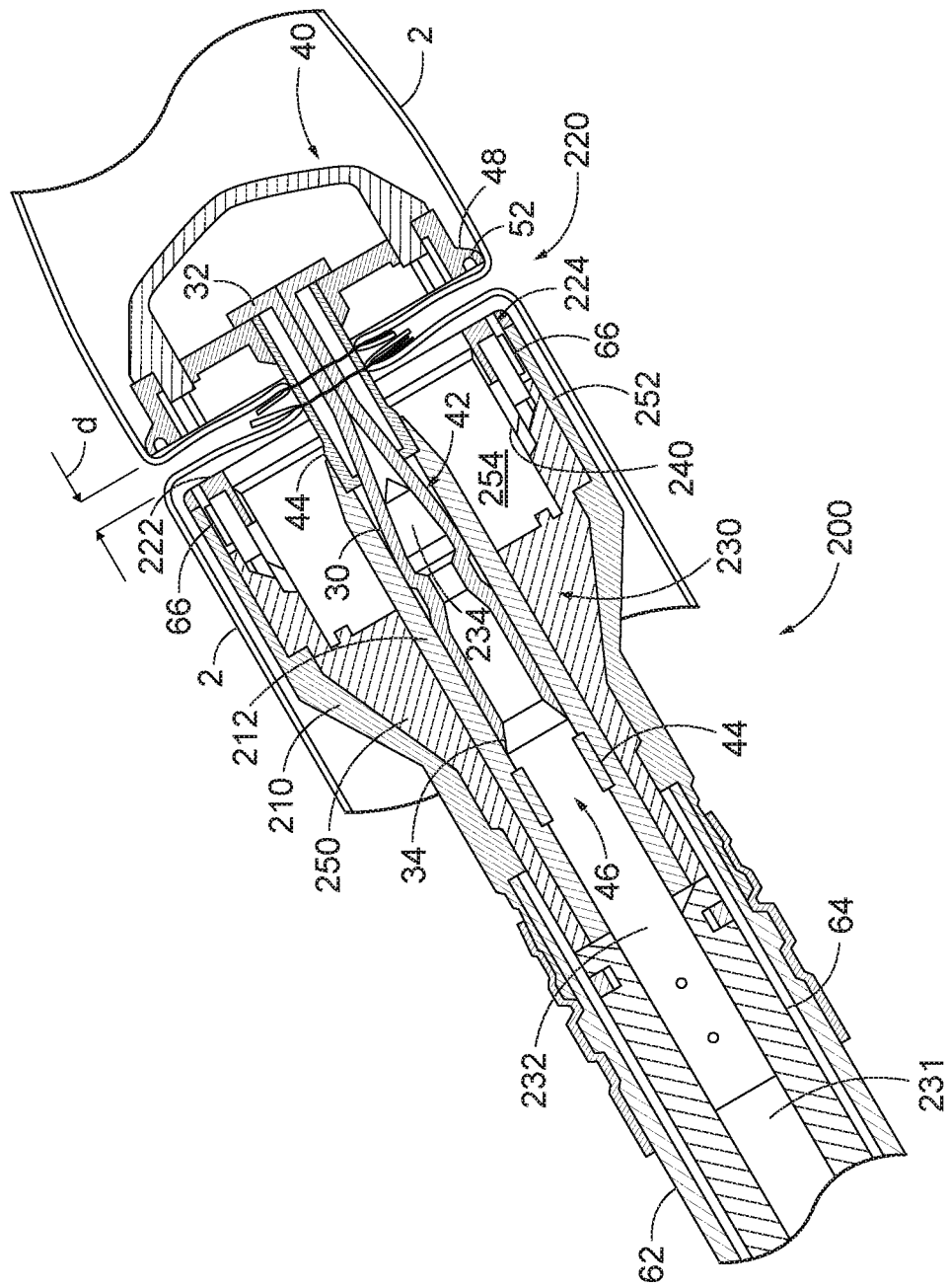
FIG. 10B depicts an enlarged longitudinal cross-sectional view of the stapling head assembly of FIG. 5, showing the anvil of FIG. 2 in a closed position, where the anvil is within the first tubular portion of tissue and the stapling head assembly is within the second tubular portion of tissue.

Staple driver member (250) is operable to actuate longitudinally within tubular casing (210) in response to rotation of trigger (74) of actuator handle assembly (70) as will be described in greater detail below. Staple driver member (250) includes two distally presented concentric annular arrays of staple drivers (252). Staple drivers (252) are arranged to correspond with the arrangement of staple forming pockets (52) described above. As best seen in FIGS. 10A-10B, each staple driver (252) is located underneath a corresponding staple (66). The arrangement of staple drivers (252) may be modified just like the arrangement of staple forming pockets (52) as described above. Staple driver member (250) also defines a bore (254) that is configured to coaxially receive core member (212) of tubular casing (210). An annular array of studs (256) project distally from a distally presented surface surrounding bore (254).

A cylindraceous knife member (240) is coaxially positioned within staple driver member (250). Knife member (240) includes a distally presented, sharp circular cutting edge (242). Knife member (240) is sized such that knife member (240) defines an outer diameter that is smaller than the diameter defined by the inner annular array of staple drivers (252). Knife member (240) also defines an opening that is configured to coaxially receive core member (212) of tubular casing (210). An annular array of openings (246) formed in knife member (240) is configured to complement the annular array of studs (256) of staple driver member (250), such that knife member (240) is fixedly secured to staple driver member (250) via studs (256) and openings (346). Therefore, when stapling driver member (250) is actuated relative to tubular casing (210), so is knife member (240). Other suitable structural relationships between knife member (240) and stapler driver member (250) will be apparent to those of ordinary skill in the art in view of the teachings herein.

A deck member (220) is fixedly secured to tubular casing (210). Deck member (220) includes a distally presented deck surface (222) defining two concentric annular arrays of staple openings (224), where each staple opening (224) has its own staple pocket (226) housing a staple (66). Staple openings (224) and staple pockets (226) are arranged to correspond with the arrangement of staple drivers (252) and staple forming pockets (52) described above. Accordingly, when staple driver member (250) is actuated distally relative to tubular casing (210) in response to rotation of trigger (74), each staple driver (252) drives a corresponding staple (66) out of its staple pocket (226) and through a corresponding staple opening (224) of deck member (220). When anvil (40) is in the closed position, staples (66) are driven into a corresponding staple forming pockets (52) to bend legs (68) of the staples (66), thereby stapling the material located between anvil (40) and stapling head assembly (200).

The arrangement of staple openings (224) may be modified just like the arrangement of staple forming pockets (52) as described above. It should also be understood that various structures and techniques may be used to contain staples (66) within stapling head assembly (200) before stapling head assembly (200) is actuated. Such structures and techniques that are used to contain staples within stapling head assembly (200) may prevent the staples from inadvertently falling out through staple openings (224) before stapling head assembly (200) is actuated. Various suitable forms that such structures and techniques may take will be apparent to those of ordinary skill in the art in view of the teachings herein.

As best seen in FIG. 6, deck member (220) defines an inner diameter that is just slightly larger than the outer diameter defined by knife member (240). Deck member (220) is thus configured to allow knife member (240) to translate distally to a point where cutting edge (242) is distal to deck surface (222).

In addition to or in lieu of the foregoing, stapling head assembly (200) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; 8,910,847, issued as U.S. Pat. No. 10,188,386 on Jan. 29, 2019; U.S. Pub. No, 2016/0374671; and/or U.S. Pub. No. 2016/0374684, issued as U.S. Pat. No. 10,226,253 on Mar. 12, 2019, the disclosures of which are incorporated by reference herein. Still other suitable configurations will be apparent to one of ordinary skill in the art in view of the teachings herein.

C. Exemplary Shaft Assembly

Stapling head assembly (200) and trocar (230) are positioned at a distal end of shaft assembly (60), as shown in FIGS. 10A-10D. Shaft assembly (60) of the present example comprises an outer tubular member (62) and a driver actuator (64). Outer tubular member (62) is coupled to tubular casing (210) of stapling head assembly (200) and to a body

Figure 7A:
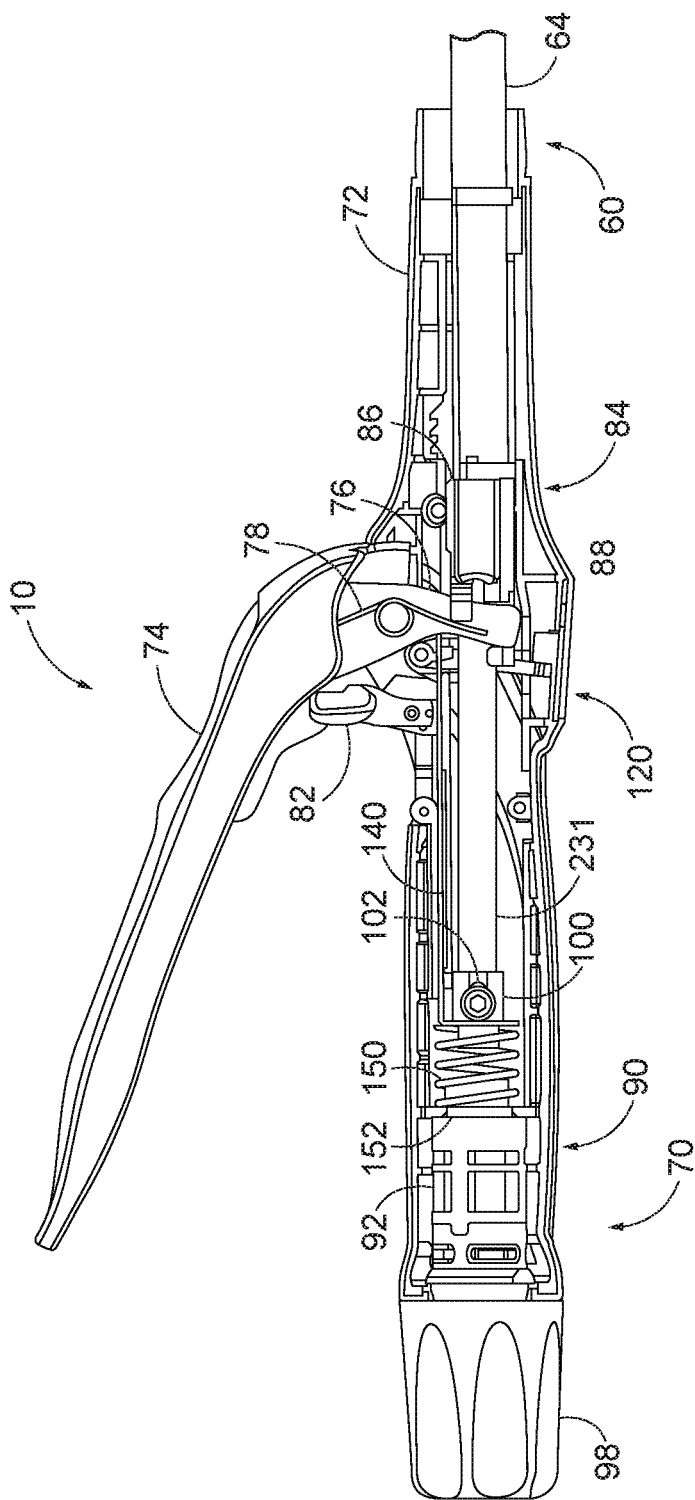
FIG. 7A depicts an enlarged side elevation view of an exemplary actuator handle assembly of the surgical instrument of FIG. 1 with a portion of the body removed, showing a trigger in an unfired position and a lockout feature in a locked position.
Figure 7B:
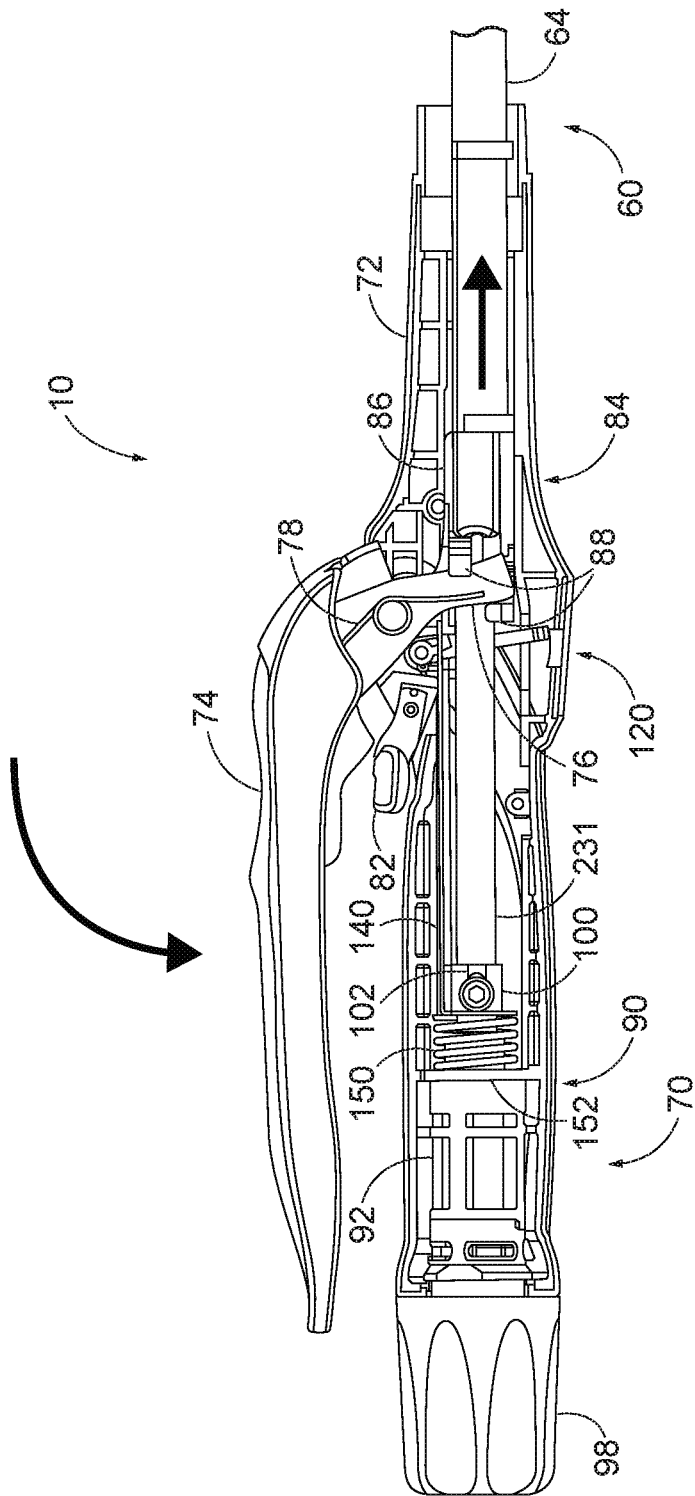
FIG. 7B depicts an enlarged side elevation view of the actuator handle assembly of FIG. 7A, showing the trigger in a fired position and the lockout feature in an unlocked position.

(72) of actuator handle assembly (70), thereby providing a mechanical ground for the actuating components therein. As seen in FIGS. 7A-7B, the proximal end of driver actuator (64) is coupled to a trigger actuation assembly (84) of actuator handle assembly (70), as described below. The distal end of driver actuator (64) is coupled to staple driver member (250) such that the rotation of trigger (74) longitudinally actuates staple driver member (250). As shown in FIGS. 10A-10D, driver actuator (64) comprises a tubular member having an open longitudinal axis such that trocar actuator (231), which is coupled to trocar (230), may actuate longitudinally within and relative to driver actuator (64). Other components may be disposed within driver actuator (64) as will be apparent to one of ordinary skill in the art in view of the teachings herein.

In the present example, shaft assembly (60) is substantially straight. However, shaft assembly (60) may extend distally from actuator handle assembly (70) with a preformed bend. In some versions, the preformed bend is configured to facilitate positioning of stapling head assembly (200) within a patient's colon. Various suitable bend angles or radii that may be used will be apparent to those of ordinary skill in the art in view of the teachings herein. In examples where shaft assembly (60) includes a preformed bend, actuator (231) may be coupled with trocar (230) via a flexible band portion (not shown). Flexible band portion (not shown) may extend from a distal end of actuator (231), located proximal to the preformed bend, to couple with trocar (230), located distal to the preformed bend. Flexible band portion (not shown) may be dimensioned to flex during translation along the longitudinal profile of the preformed bend of shaft assembly (60). In such cases, trocar actuator (231) may be slidably housed within actuator handle assembly (70), while trocar (230) is slidably housed within tubular casing (210). Flexible band portion (not shown) may be connected to both trocar (230) and actuator (231) via pins.

Shaft assembly (60) may be further constructed in accordance with at least some of the teachings of U.S. Pat. Nos. 5,205,459; 5,271,544; 5,275,322; 5,285,945; 5,292,053; 5,333,773; 5,350,104; 5,533,661; U.S. Pub. No. 2012/0292372, issued as U.S. Pat. No. 8,910,847 on Dec. 16, 2014; and/or U.S. Pub. No. 2015/0083773, issued as U.S. Pat. No. 9,936,949 on Apr. 10, 2018, the disclosures of which are incorporated by reference herein; and/or in accordance with other configurations as will be apparent to one of ordinary skill in the art in view of the teachings herein.

D. Exemplary Actuator Handle Assembly

Referring now to FIGS. 7A-8, actuator handle assembly (70) comprises a body (72), a trigger (74), a lockout feature (82), a trigger actuation assembly (84), and a trocar actuation assembly (90). Trigger (74) of the present example is pivotably mounted to body (72) and is coupled to trigger actuation assembly (84) such that rotation of trigger (74) from an unfired position (shown in FIG. 7A) to a fired position (shown in FIG. 7B) actuates driver actuator (64) described above. A spring (78) is coupled to body (72) and trigger (74) to bias trigger (74) towards the unfired position. Lockout feature (82) is a pivotable member that is coupled to body (72). In a first, locked position, as shown in FIG. 7A, lockout feature (82) is pivoted upwards and away from body (72) such that lockout feature (82) engages trigger (74) and mechanically resists actuation of trigger (74) by a user. In a second, unlocked position, such as that shown in FIGS. 1 and 7B, lockout feature (82) is pivoted downward such that trigger (74) may be actuated by the user. Accordingly, with lockout feature (82) in the second position, trigger (74) can engage a trigger actuation assembly (84) to fire instrument F.

As shown in FIGS. 7A-7B, trigger actuation assembly (84) of the present example comprises a slidable trigger carriage (86) engaged with a proximal end of driver actuator (64). Carriage (86) includes a set of tabs (88) on a proximal end of carriage (86) to retain and engage a pair of trigger arms (76) extending from trigger (74). Accordingly, when trigger (74) is pivoted, carriage (86) is actuated longitudinally and transfers the longitudinal motion to driver actuator (64). In the example shown, carriage (86) is fixedly coupled to the proximal end of driver actuator (64), though this is merely optional. Indeed, in one merely exemplary alternative, carriage (86) may simply abut driver actuator (64) while a distal spring (not shown) biases driver actuator (64) proximally relative to actuator handle assembly (70).

Trigger actuation assembly (84) may be further constructed in accordance with at least some of the teachings of U.S. Pat. Nos. 5,205,459; 5,271,544; 5,275,322, 5,285,945; 5,292,053; 5,333,773; 5,350,104; 5,533,661; U.S. Pub. No. 2012/0292372, issued as U.S. Pat. No. 8,910,847 on Dec. 16, 2014; and/or U.S. Pub. No. 2015/0083773, issued as U.S. Pat. No. 9,936,949 on Apr. 10, 2018 the disclosures of which are incorporated by reference herein; and/or in accordance with other configurations as will be apparent to one of ordinary skill in the art in view of the teachings herein.

Body (72) also houses trocar actuation assembly (90) configured to actuate trocar (230) longitudinally in response to rotation of adjustment knob (98). As best shown in FIGS. 7A-8, trocar actuation assembly (90) of the present example comprises adjustment knob (98), a grooved shank (94), and a sleeve (92). Grooved shank (94) of the present example is located at a proximal end of trocar actuator (231). In other versions grooved shank (94) and trocar actuator (231) may alternatively be separate components that engage to transmit longitudinal movement. While grooved shank (94) is configured to translate within body (72), grooved shank (94) does not rotate within body (72). Adjustment knob (98) is rotatably supported by the proximal end of body (72) and is operable to rotate sleeve (92), which is engaged with grooved shank (94) via an internal tab (not shown). Adjustment knob (98) also defines internal threading (not shown) as will be described in greater detail below. Grooved shank (94) of the present example comprises a continuous groove (96) formed in the outer surface of grooved shank (94). Accordingly, when adjustment knob (98) is rotated, the internal tab of sleeve (92) rides within groove (96) and grooved shank (94) is longitudinally actuated relative to sleeve (92). Since grooved shank (94) is located at the proximal end of trocar actuator (231), rotating adjustment knob (98) in a first direction advances trocar actuator (231) distally relative to actuator handle assembly (70). When trocar (230) is coupled with anvil (40), anvil (40) also advances distally relative to stapling head assembly (200) thereby increasing the distance between proximal surface (50) of the anvil (40) and distally presented deck surface (222) of deck member (220), otherwise known as a gap distance d. By rotating adjustment knob (98) in the opposite direction, trocar actuator (231) is actuated proximally relative to actuator handle assembly (70) to reduce the gap distance d between anvil (40) and stapling head assembly (200) when trocar (230) is coupled with anvil (40). Thus, trocar actuation assembly (90) is operable to actuate trocar (230) in response to rotating adjustment knob (98). Other configurations for trocar actuation assembly (90) will be apparent to one of ordinary skill in the art in view of the teachings herein.

Groove (96) of the present example comprises a plurality of different portions (96A, 96B, 96C) that have a varying pitch or number of grooves per axial distance. The present groove (96) is divided into a distal portion (96A), a middle portion (96B) and a proximal portion (96C). As shown in FIG. 5, distal portion (96A) comprises a fine pitch or a high number of grooves over a short axial length of grooved shank (94). Middle portion (96B) comprises a section with comparably coarser pitch or fewer grooves per axial length such that relatively few rotations are required for the internal tab of sleeve (92) to traverse along axial distance. When anvil (40) is in an initial, distal position in relation to stapling head assembly (200) (as shown in FIG. 10A) the internal tab of sleeve (92) is positioned in middle portion (96B). Accordingly, the gap distance d may be quickly reduced through relatively few rotations of adjustment knob (98) while the internal tab of sleeve (92) traverses middle portion (96B). Proximal portion (96C) of the present example is substantially like distal portion (96A) and comprises a fine pitch or a high number of grooves over a short axial distance of grooved shank (94) such that many rotations are required to traverse the short axial distance. Proximal portion (96C) of the present example is engaged by the internal threading defined by knob (98) when anvil (40) is substantially near to stapling head assembly (200) (as shown in FIG. 10B), such that indicator bar (110) moves within indicator window (120) along scale (130) to indicate that the anvil gap is within a desired operating range, as will be described in more detail below. Accordingly, when grooved shank (94) reaches a proximal position where the proximal portion (96C) of groove (96) engages the internal threading of knob (98), each rotation of adjustment knob (98) may reduce the gap distance d by a relatively small amount to provide for fine tuning. The internal tab of sleeve (92) may be disengaged from groove (96) when proximal portion (96C) is engaged with the internal threading of knob (98).

Trocar actuation assembly (90) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pub. No. 2015/0083773, issued as U.S. Pat. No. 9,936,949 on Apr. 10, 2018, the disclosures of which are incorporated by reference herein; and/or in accordance with other configurations as will be apparent to one of ordinary skill in the art in view of the teachings herein.

As noted above, gap distance d corresponds to the distance between anvil (40) and stapling head assembly (200). When instrument (10) is inserted into a patient, this gap distanced may not be easily viewable. Accordingly, a moveable indicator bar (110), shown in FIGS. 8-9, is provided to be visible through an indicator window (120) positioned opposite to trigger (74). As will be described in greater detail below, indicator bar (110) is operable to move in response to rotation of adjustment knob (98) such that the position of indicator bar (110) is representative of the gap distance d. As shown in FIG. 9, indicator window (120) further comprises a scale (130) which indicates that the anvil gap is within a desired operating range (e.g., a green colored region or "green zone") and a corresponding staple compression representation at each end of scale (130). By way of example only, as shown in FIG. 9, a first staple image (132) depicts a large staple height while a second staple image (134) depicts a small staple height. Accordingly, a user can view the position of the coupled anvil (40) relative to the stapling head assembly (200) via indicator bar (110) and scale (130). The user may then adjust the positioning of anvil (40) via adjustment knob (98) accordingly.

In the example shown in FIGS. 7A-8, a U-shaped clip (100) is attached to an intermediate portion of trocar actuator (231) located distally of grooved shank (94). In the present example, an extension of trocar actuator (231) engages a slot in the housing of handle assembly (70) to prevent trocar actuator (231) from rotating about its axis when adjustment knob (98) is rotated.

Because trocar actuator (231) and trocar (230) are two separate components joined together during assembly, a tolerance stack may occur once trocar (230) and trocar actuator (231) are assembled and suitably incorporated into instrument (10). To accommodate for this potential tolerance stack, it may be necessary to calibrate the proper placement of trocar actuator (231) within instrument (10) such that indicator bar (110) may show a proper gap distance d during exemplary use. U-shaped clip (100) of the present example further includes an elongated slot (102) on each of its opposite sides for receiving an attachment member, such as a screw, bolt, pin, etc., to selectively adjust the longitudinal position of elongated slot (102) of U-shaped clip (100) relative to trocar actuator (231) for purposes of calibrating indicator bar (110) relative to scale (130). In some versions, the attachment member (e.g., screw, bolt, pin, etc.) engages with a portion of body (72) to substantially prevent trocar actuator (231) from rotating about its axis when adjustment knob (98) is rotated.

As shown in FIG. 8, actuator handle assembly (70) further includes an indicator bracket (140) configured to engage and pivot an indicator (104). Indicator bracket (140) of the present example is slidable relative to body (72) along a pair of slots formed on body (72). Indicator bracket (140) comprises a rectangular plate (144), an indicator arm (146), and an angled flange (142). Angled flange (142) is formed at the proximal end of rectangular plate (144) and includes an aperture (not shown) to slidable mount onto trocar actuator (231) and/or grooved shank (94). A coil spring (150) is interposed between flange (142) and a boss (152) to bias flange (142) against U-shaped clip (100). Accordingly, when U-shaped clip (100) actuates distally with trocar actuator (231) and/or grooved shank (94), coil spring (150) urges indicator bracket (140) to travel distally with U-shaped clip (100). In addition, U-shaped clip (100) urges indicator bracket (140) proximally relative to boss (152) when trocar actuator (231) and/or grooved shank (94) translate proximally, thereby compressing coil spring (150). In some versions indicator bracket (140) may be fixedly attached to trocar actuator (231) and/or grooved shank (94).

In the present example, a portion of lockout feature (82) abuts a surface (141) of indicator bracket (140) when indicator bracket (140) is in a longitudinal position that does not correspond to when gap distance d is within a desired operating range (e.g., a green colored region or "green zone"). When gap distance d is within a desired operating range (e.g., a green colored region or "green zone"), indicator bracket (140) narrows to provide a pair of gaps (145) on either side of an indicator arm (146) that permits lockout feature (82) to pivot, thereby releasing trigger (74). Accordingly, lockout feature (82) and indicator bracket (140) can substantially prevent a user from releasing and operating trigger (74) until anvil (40) is in a predetermined operating range. Lockout feature (82) may be omitted entirely in some versions.

This operating range may be visually communicated to the user via an indicator bar (110) of an indicator (104)

shown against a scale (130), described briefly above. At the distal end of indicator bracket (140) is a distally projecting indicator arm (146) which terminates at a laterally projecting finger (148) for controlling the movement of indicator (104). Indicator arm (146) and finger (148), best shown in FIG. 5, are configured to engage a tab (106) of indicator (104) such that indicator (104) is pivoted when indicator bracket (140) is actuated longitudinally. In the present example, indicator (104) is pivotably coupled to body (72) at a first end of indicator (104), though this is merely optional and other pivot points for indicator (104) will be apparent to one of ordinary skill in the art in view of the teachings herein. An indicator bar (110) is positioned on the second end of indicator (104) such that indicator bar (110) moves in response to the actuation of indicator bracket (140). Accordingly, as discussed above, indicator bar (110) is displayed through an indicator window (120) against a scale (130) (shown in FIG. 6) to show the relative gap distance d between proximal surface (50) of anvil (40) and distally presented deck surface (222) of deck member (220).

Of course indicator bracket (140), indicator (104), and/or actuator handle assembly (70) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pub. No. 2012/0292372, issued as U.S. Pat. No. 8,910,847 on Dec. 16, 2014; and/or U.S. Pub. No. 2015/0083773, issued as U.S. Pat. No. 9,936,949 on Apr. 10, 2018the disclosures of which are incorporated by reference herein; and/or in accordance with other configurations as will be apparent to one of ordinary skill in the art in view of the teachings herein.

E. Exemplary Use of Circular Stapling Surgical Instrument

FIGS. 7A-7B and FIGS. 10A-10E show an exemplary use of circular stapling surgical instrument (10) in accordance with the description above. As mentioned above, anvil (40) may selectively couple with trocar (230) such that movement of trocar (230) relative to tubular casing (210) and deck member (220) leads to movement of anvil (40) relative to tubular casing (210) and deck member (220). With anvil (40) as a separate component, it should be understood that anvil (40) may initially be inserted and secured to a portion of tissue (2) prior to being coupled with trocar (230). By way of example only, anvil (40) may be inserted into and secured to a first tubular portion of tissue (2) while stapling head assembly (200) is inserted into and secured to a second tubular portion of tissue (2). For instance, the first tubular portion of tissue (2) may be sutured to or about a portion of anvil (40), and the second tubular portion of tissue (2) may be sutured to or about trocar (230).

As shown in FIG. 10A, anvil (40) may then be coupled to trocar (230) in accordance with the description above, such as a snap fitting between latch members (30) of anvil (40) and head (234) of trocar (230). In FIG. 10A, trocar (230) is shown in a distal most actuated position. Trocar (230) may be actuated to the distal most actuated position by rotation of knob (98) in accordance with the description above. Such an extended position for trocar (230) may provide a larger area to which tissue (2) may be coupled prior to attachment of anvil (40). The extended position of trocar (230) may also provide for easier attachment of anvil (40) to trocar (230). At the position shown in FIG. 10A, trigger (74) is locked in the position shown in FIG. 7A by lockout feature (82), as lockout feature (82) may not pivot to unlock trigger (74) due to interference caused by surface (141) of indicator bracket (140) in accordance with the description above.

As mentioned above, when anvil (40) is coupled to trocar (230), rotation of adjustment knob (98) may translate both trocar (230) and anvil (40), thereby enlarging or reducing gap distance d. For instance, as shown sequentially in FIGS. 10A-10B, anvil (40) is shown actuating proximally relative to actuator handle assembly (70) from an initial, open position (FIG. 10A) to a closed position (FIG. 10B) where gap distance d is brought within a suitable predetermined range. When gap distance d is brought within a suitable predetermined range, indicator bar (110) may move within indicator window (120) to show the relative gap distance d is within a desired operating range (e.g. a green colored region or "green zone") in accordance with the description above. Additionally, shown between FIGS. 7A-7B, when gap distance d is brought within a suitable predetermined range, lockout feature (82) may be pivoted relative to body (72) to an unlocked position and trigger (74) may pivot relative to body (72) to engage trigger actuation assembly (84) in accordance with the description above.

Figure 10C:
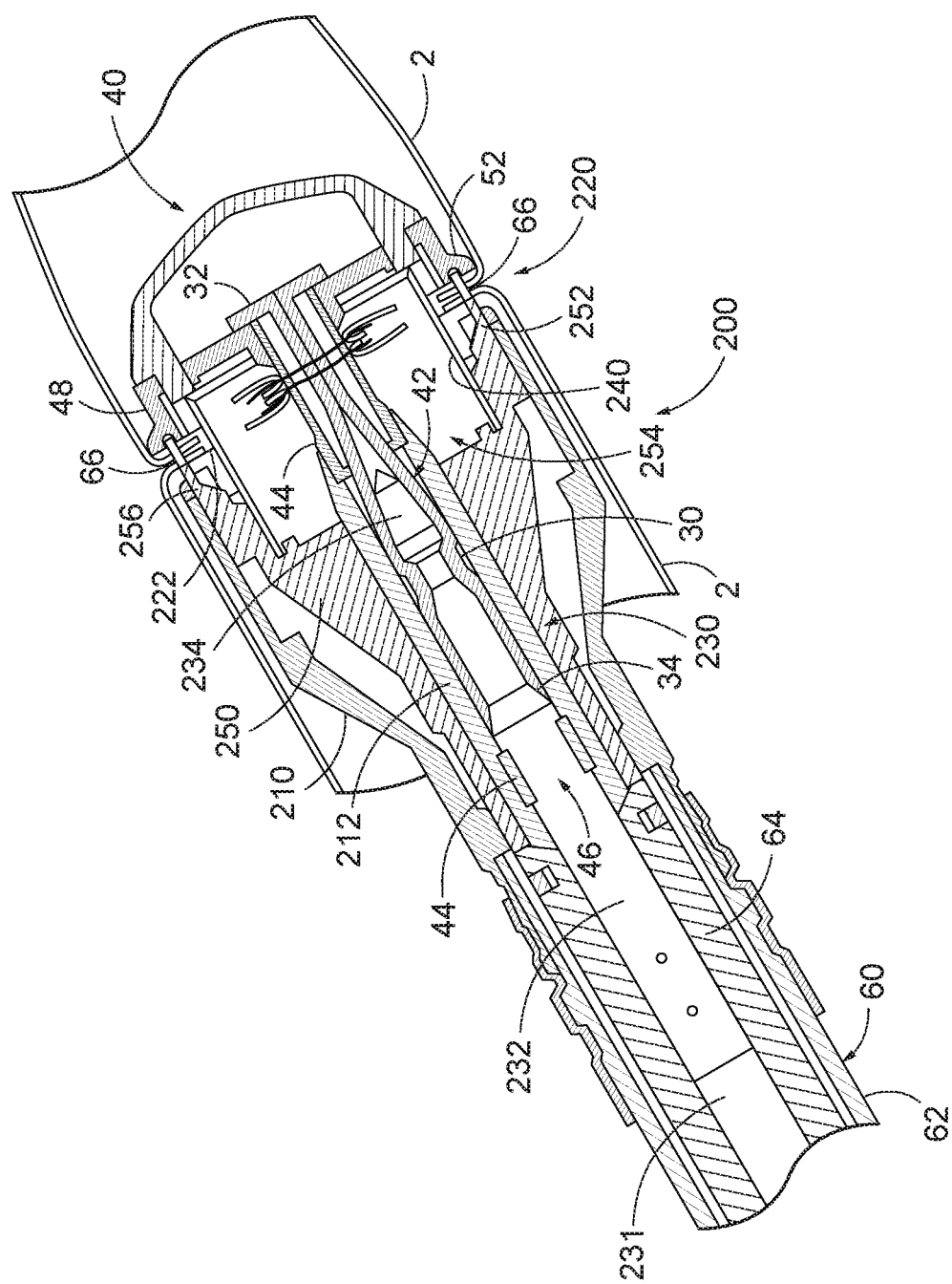
FIG. 10C depicts an enlarged longitudinal cross-sectional view of the stapling head assembly of FIG. 5, showing the anvil of FIG. 2 in the closed position, were an exemplary staple driver and blade are in a fired position such that the first tubular portion of tissue and the second tubular portion of tissue are stapled together with excess tissue severed.

As shown in FIG. 7B, with lockout feature (82) pivoted into the unlocked position, trigger (74) is pivoted toward body (72) such that trigger arms (76) drive against tabs (88) to distally actuate slidable trigger carriage (86) and driver actuator (64). As shown in FIG. 10C, distal actuation of driver actuator (64) drives slidable staple driver member (250), staples drivers (252), and cylindraceous knife member (240) distally. Distal advancement of staple drivers 9352) drive staples (66) against corresponding staple forming pockets (52) thereby stapling tissue (2) between anvil (40) and stapling head assembly (200) to form a continuous tubular portion of tissue (2). Additionally, distal advancement of cylindraceous knife member (240) severs excess tissue located radially interior to newly formed staples (66). Stapling head assembly (200) is operable to staple and sever tissue (2) by a user pivoting a trigger (74) of actuator handle assembly (70), as will be described in greater detail below.

Figure 10D:
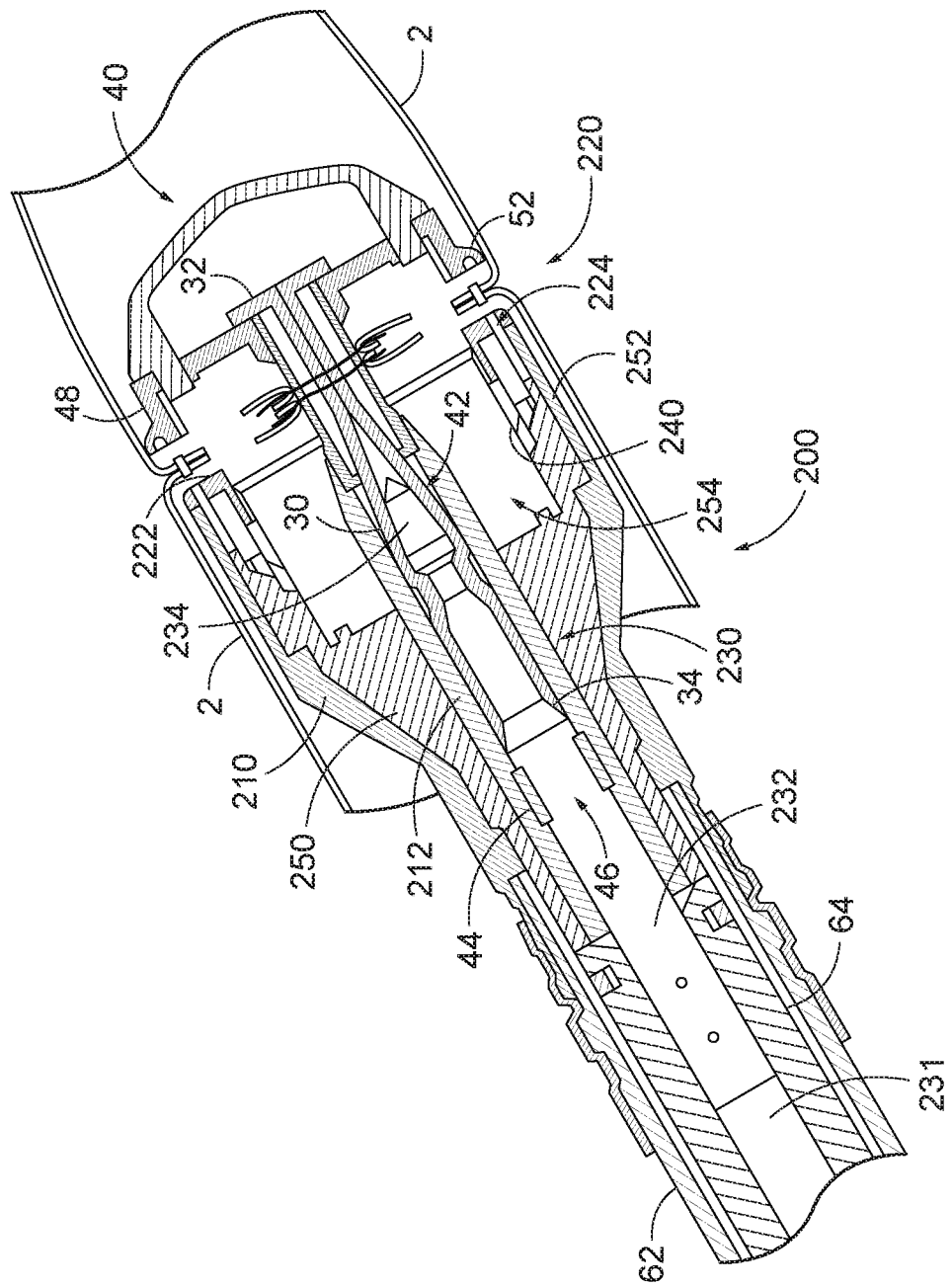
FIG. 10D depicts an enlarged longitudinal cross-sectional view of the stapling head assembly of FIG. 5, showing the anvil of FIG. 2 in a second open position, where the first tubular portion of tissue and the second tubular portion of tissue are attached.
Figure 10E:
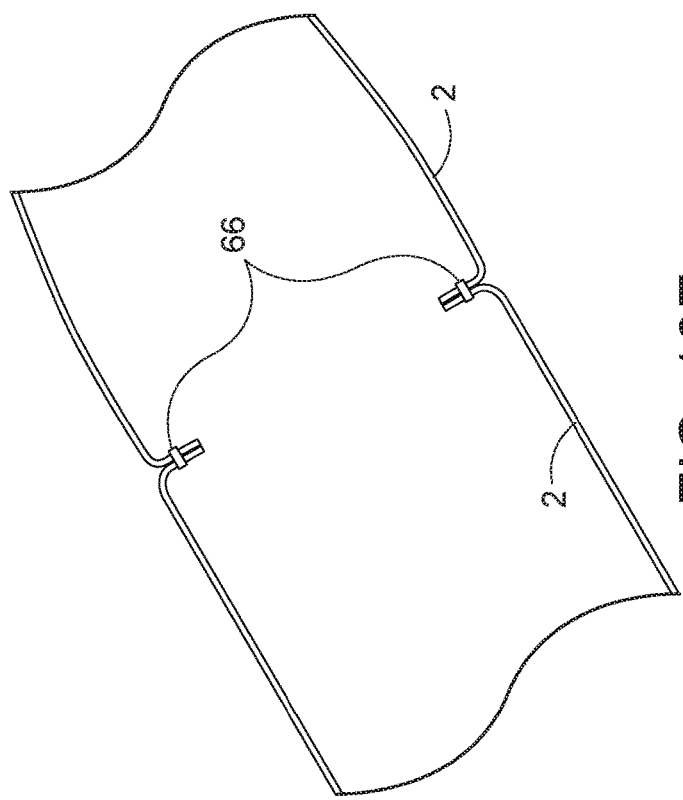
FIG. 10E depicts an enlarged longitudinal cross-section view of the first tubular portion and the second tubular portion after the stapling head assembly of FIG. 5 and the anvil of FIG. 2 have been removed, leaving a completed end-to-end anastomosis.
Figure 11:
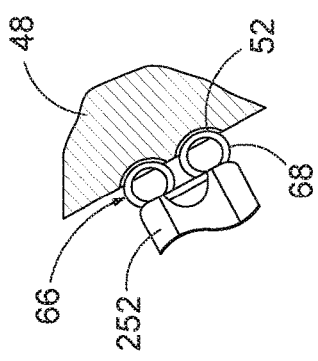
FIG. 11 depicts an enlarged partial cross-sectional view of an exemplary staple formed against the anvil of FIG. 2.

As best shown in FIG. 10D, once trigger (74) has been actuated to staple and sever tissue (2), a user may then turn rotatable knob (98) to distally advance anvil (40), thereby releasing portions of tissue (2) grasped between proximal surface (50) of anvil (40) and distally presented deck surface (222) of deck member (220). As best shown in FIG. 10E, with previously grasped tissue (2) released, a user may then remove instrument (10), thereby leaving a continuous tubular portion of tissue (2) behind.

II. Exemplary Alternative Anvil with Shank Having Unitary Latches

As described above, anvil (40) includes pivoting latch members (30) that are configured to selectively couple anvil (40) with trocar (230). When trocar (230) and anvil (40) are properly coupled, actuation of trocar (230) may drive actuation of anvil (40) via the coupling between trocar head (234) and latch members (30). Additionally, movement of trocar actuator (231) and indicator bracket (140) pivots indicator (104) to visually display the gap distance d between deck member (220) and proximal surface (50) of anvil (40). In other words, the longitudinal location of trocar actuator (231) may be used to visually display the gap distance d between deck member (220) and proximal surface (50) of anvil (40) when anvil (40) is properly coupled with trocar (230).

Because latch members (30) couple anvil (40) with trocar (230), and because the longitudinal location of trocar actuator (231) relative to handle assembly (70) is used to visually represent the gap distance d between deck member (220) and proximal surface (50) of anvil (40), a consistent and uniform distance between latch members (30) and the rest of anvil (40) may be desirable. If the actual distance between pivoting latch members (30) and proximal surface (50) of anvil (40) deviates from the assumed distance between pivoting latch members (30) and proximal surface (50) (i.e. a tolerance stack), then the actual distance between trocar actuator (231) and proximal surface (50) of anvil (40) will also deviate from the assumed distance. If this tolerance stack is too great, indicator (104) may display an inaccurate gap distance d during exemplary use. If the operator actuates stapling head assembly (200) based on an inaccurately indicated gap distance d, and the actual gap distance d is above or below an acceptable range, the result may be undesirable.

As also described above, pivoting latch members (30) include a "T" shaped distal end (32) that helps secure latch members (30) within bore (46). Therefore, pivoting latch members (30) are separate pieces that are individually attached within bore (46) of shank (44). Because pivoting latch members (30) are separate pieces that are later attached to the rest of anvil (40), an undesirable tolerance stack may occur if pivoting latch members (30) are improperly formed, improperly attached, somehow become lose, or provide some other undesirable result. Therefore, it may be desirable to form and use an anvil having latch members that are integrally formed with the rest of the anvil, or at least the shank.

Figure 12:
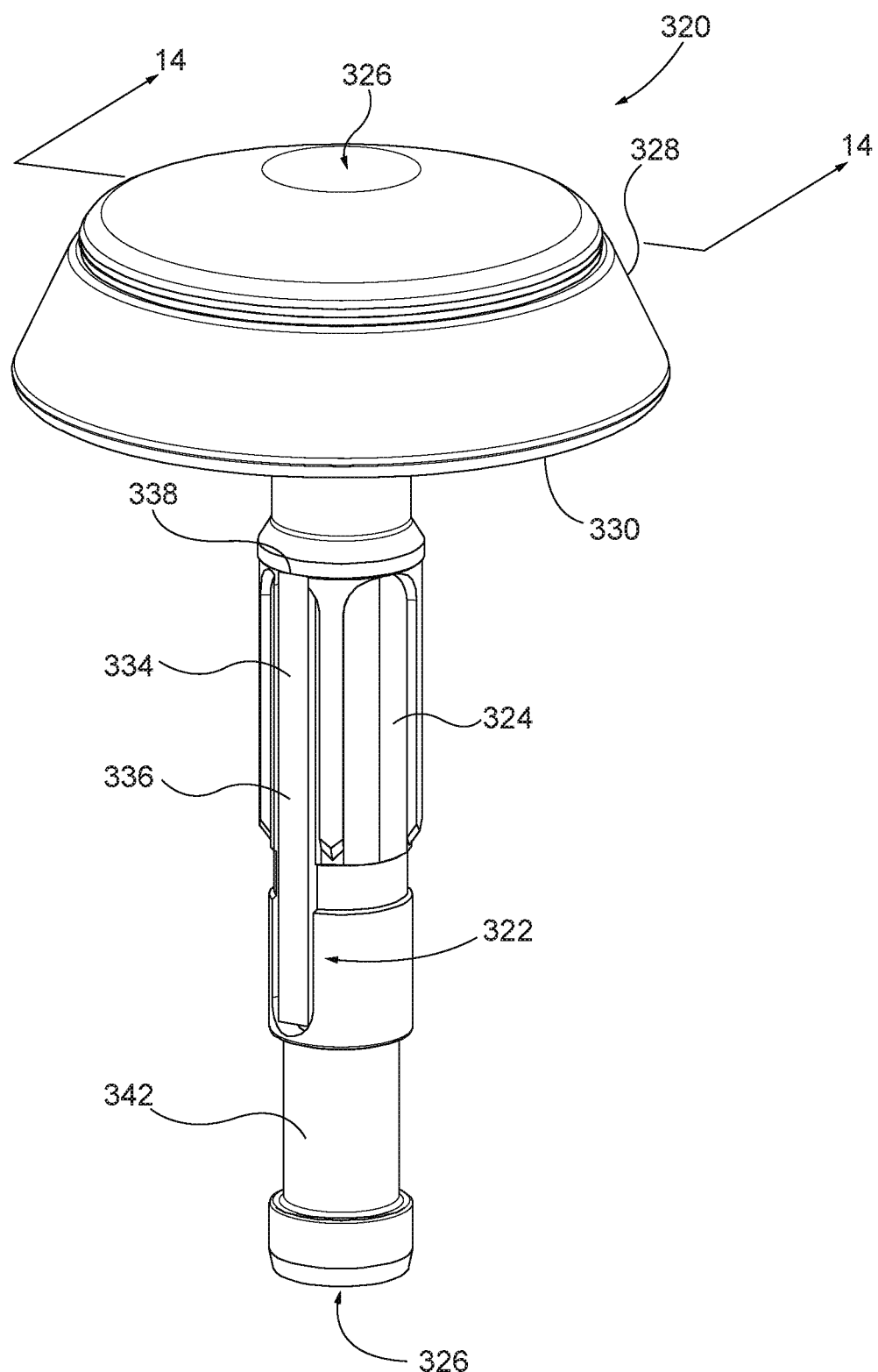
FIG. 12 depicts a perspective view of an exemplary alternative anvil that may be readily incorporated into the surgical instrument of FIG. 1.
Figure 13:
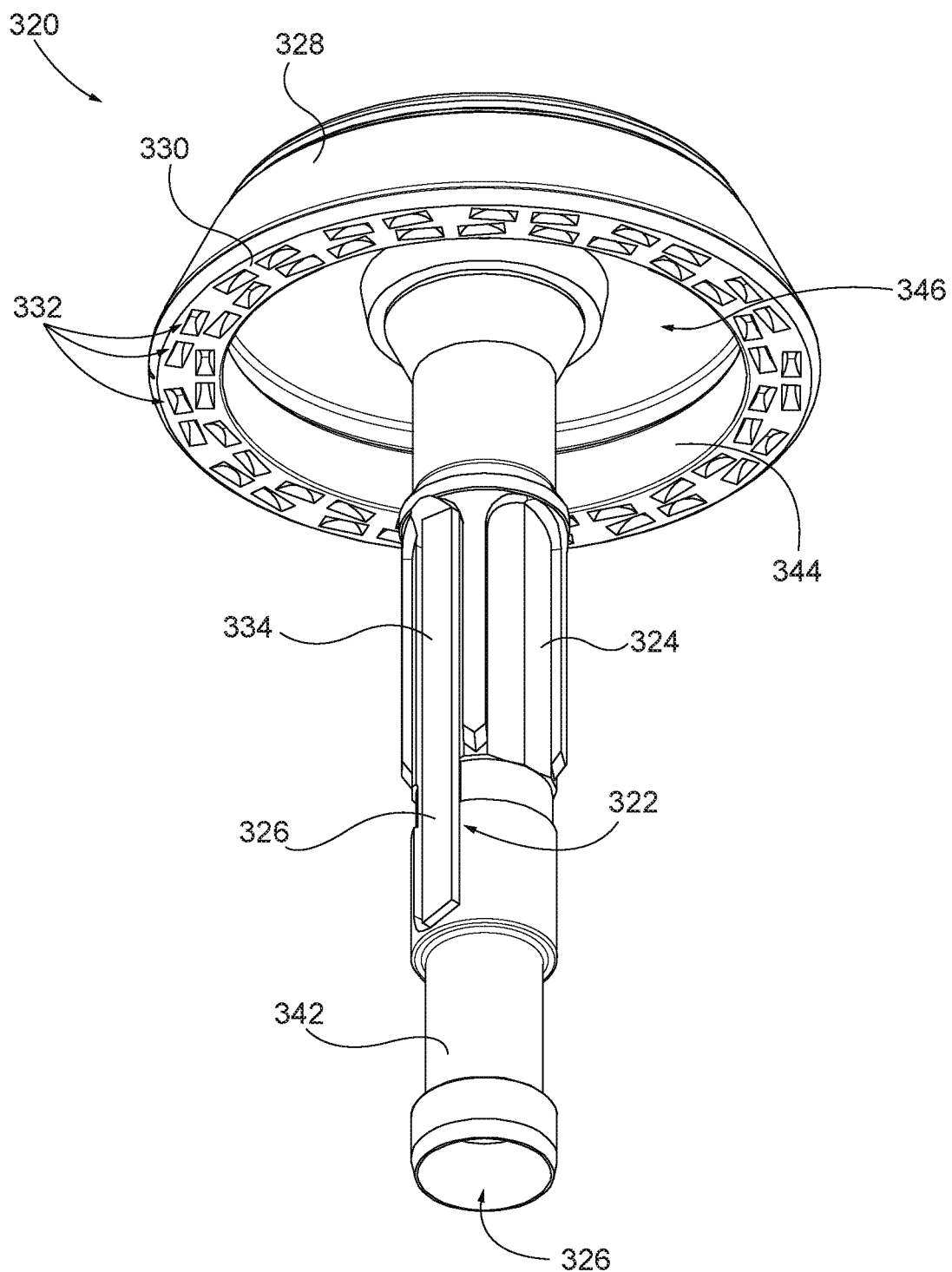
FIG. 13 depicts another perspective view of the anvil of FIG. 12.
Figure 14:
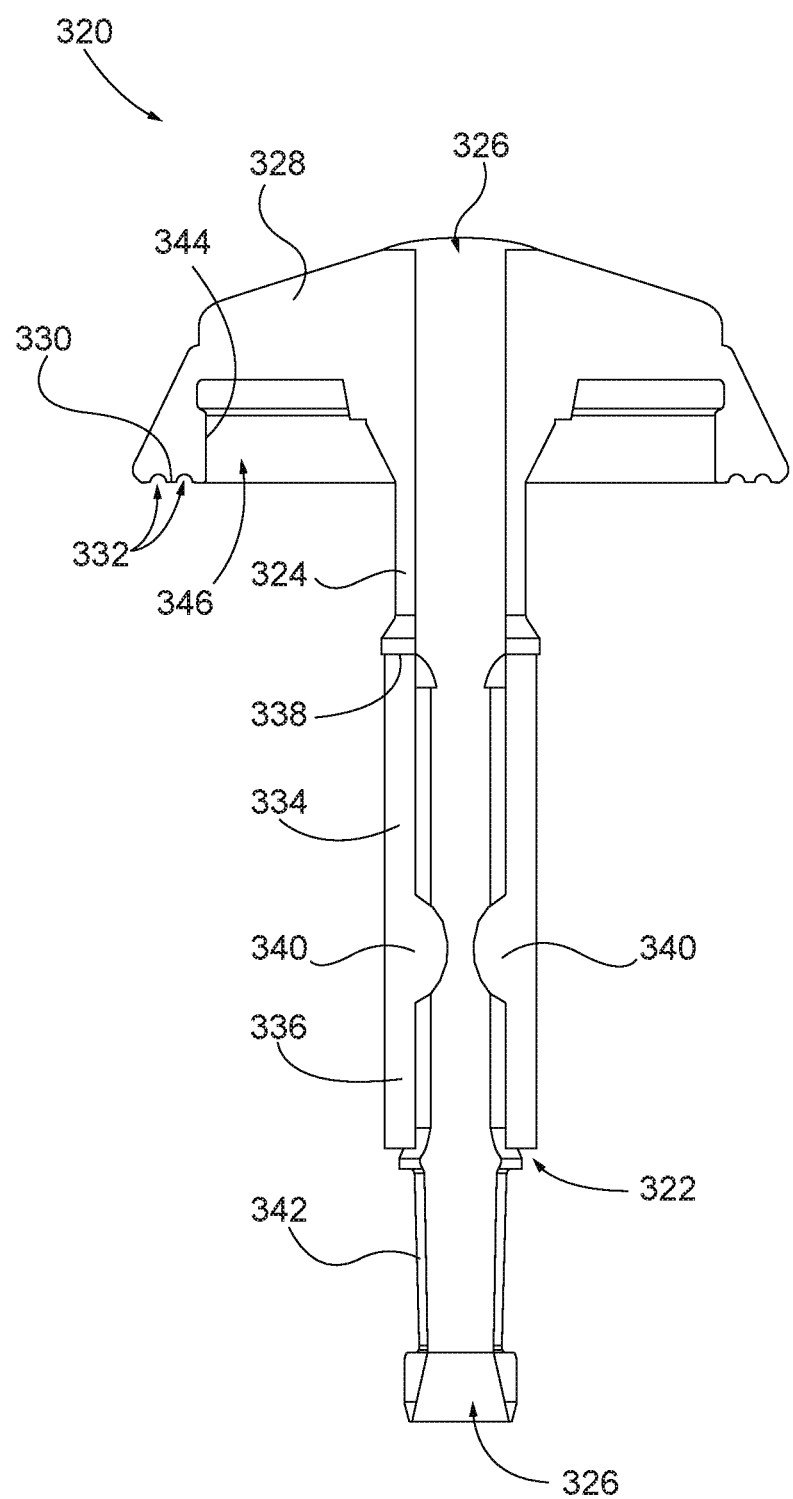
FIG. 14 depicts a cross-sectional view of the anvil of FIG. 12, taken along line 14-14 of FIG. 12.

FIGS. 12-14 show an exemplary anvil (320) having integral pivoting latch members (330) that may help reduce or eliminate the unwanted tolerance stack described above. Anvil (320) may be readily incorporated into instrument (10) in replacement of anvil (40) described above. Therefore, anvil (320) of the present example may selectively couple to trocar (230) such that when coupled, movement of trocar (230) relative to stapling head assembly (200) also moves anvil (320) relative to stapling head assembly (200). Anvil (320) includes a head (328) and a shank (324), which maybe substantially like head (48) and shank (44) described above, with differences described below. Head (328) and shank (324) may be made from a single piece of material such that head (328) and shank (324) are machined, or otherwise formed, into their respective shapes. Because head (328) and shank (324) are formed from a single piece of material, a potential tolerance stack accumulated from joining the two pieces may be reduced or eliminated.

Head (328) includes a proximal surface (330) that defines a plurality of staple forming pockets (332), which may be substantially like proximal surface (50) and staple forming pockets (52) described above. Staple forming pockets (332) are arranged in two concentric annular arrays. In some other versions, staple forming pockets (332) are arranged in three or more concentric annular arrays. Staple forming pockets (332) are configured to deform staples as the staples are driven into staple forming pockets (332). Accordingly, when anvil (320) is in the closed position and staples (66) are driven out of stapling head assembly (200) into staple forming pockets (332), each staple forming pocket (332) may deform a generally "U" shaped staple (66) into a "B" shape as is known in the art. As best seen in FIG. 13, proximal surface (330) terminates at an inner edge (344), which defines an outer boundary of an annular recess (346) surrounding shank (324). Inner edge (344) and annular recess (346) are substantially like inner edge (54) and annular recess (56) described above.

Shank (324) extends proximally from head (328). In the current example, shank (324) includes a necked down portion (342). Necked down portion (342) may act as a gripping portion of shank (324) such that an operator may utilizes any suitable tool (e.g., conventional grasping instrument) to better grasp and manipulate anvil (320) during an exemplary procedure. While necked down portion (342) is included in this example, it should be understood that necked down portion (342) is entirely optional.

As best seen in FIG. 14, shank (324) and head (328) define a bore (326) that is dimensioned to receive portions of trocar (232), more specifically, head (234) and the reduced outer diameter portion of shaft (232). Shank (324) also defines a pair of lateral openings (322). Additionally, shank (324) includes a pair of integral pivoting latch members (334). Integral pivoting latch members (334) each include a proximally extending arm (336) located within lateral openings (322) and a latch shelf (340) extending from an interior of arm (336) radially inward within bore (326).

Arms (336) are coupled to a distal end of respective lateral openings (332) via a living hinge (338). As used herein, the term "living hinge" means a hinge that is unitarily formed of the same material as the two pieces the hinge connects. Integral pivoting latch members (334), living hinges (338), and shank (324) all thus consist of a homogenous continuum of material. The integral pivoting latch members (334) are operable to pivot about living hinge (338) radially toward and away from lateral openings (322) to selectively couple with trocar (230). Therefore, lateral openings (322) provide clearance for arms (336) and latch shelves (340) to deflect radially outwardly away from the longitudinal axis defined by shank (324). However, arms (336) are resiliently biased radially inwardly toward the longitudinal axis defined by shank (324) such that latch shelves (340) are located within bore (326). Like latch shelves (36) described above, latch shelves (340) have a complementary position and configuration with proximal surface (238) of head (234) such that latch shelves (340) engage proximal surface (238) when shank (324) of anvil (320) is fully seated on trocar (230). Integral pivoting latch members (334) thus act as retaining clip to allow anvil (320) to be selectively secured to trocar (230) of stapling head assembly (200).

Integral pivoting latch members (334) are formed from material originally forming shank (324) such that lateral openings (322) are defined when integral pivoting latch members (334) are cut or otherwise formed from shank (324). Because integral pivoting latch members (334) are formed from material originally forming shank (324) rather than if latch members (334) were separate pieces, potential tolerance stacks associated with latch members (334) relative to shank (324) and head (238) may be reduced or eliminated.

Figure 15A:
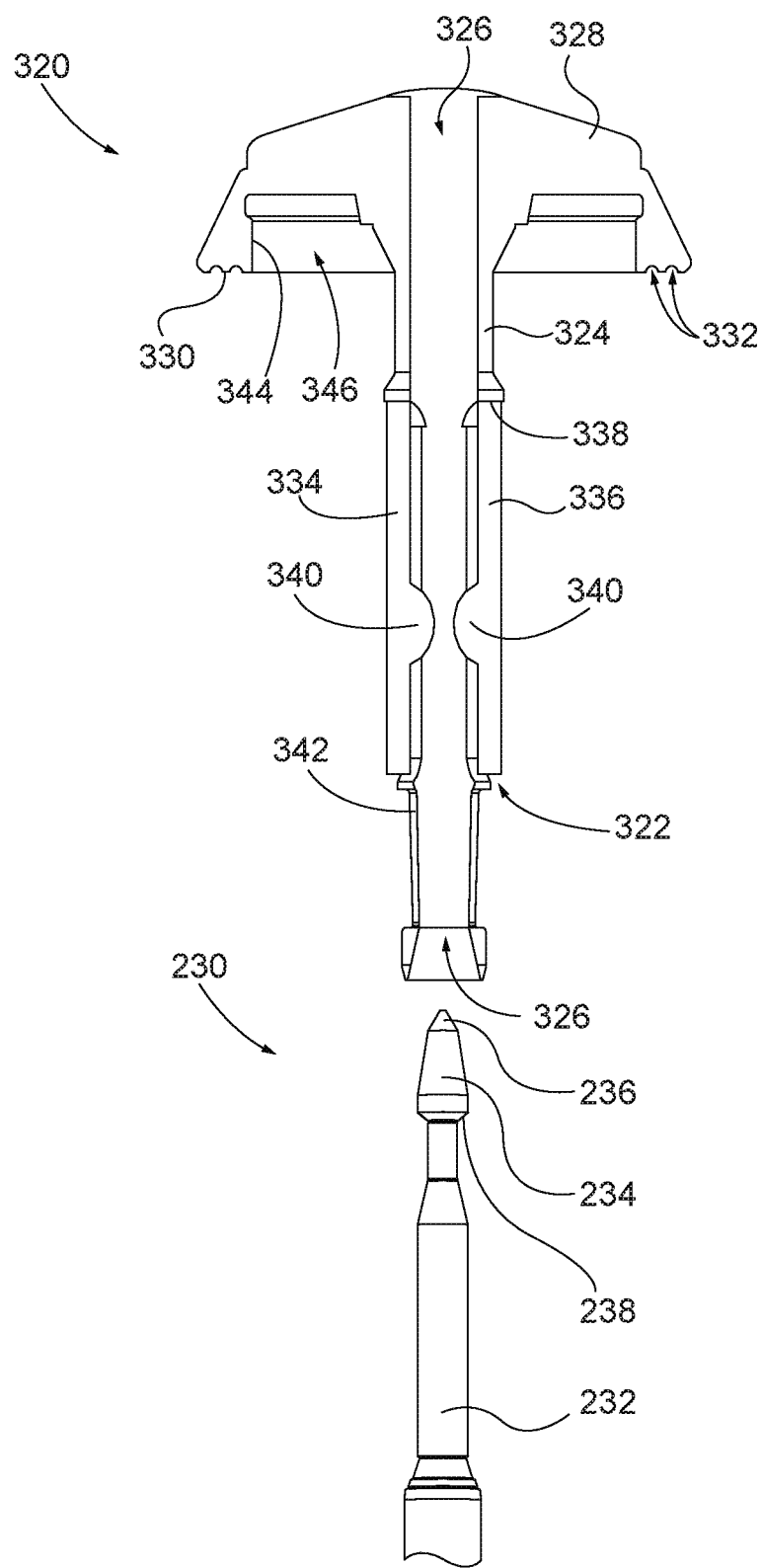
FIG. 15A depicts a cross-sectional view a trocar of the stapling head assembly of FIG. 5 aligned for coupling with the anvil of FIG. 12, taken along line 14-14 of FIG. 12.
Figure 15B:
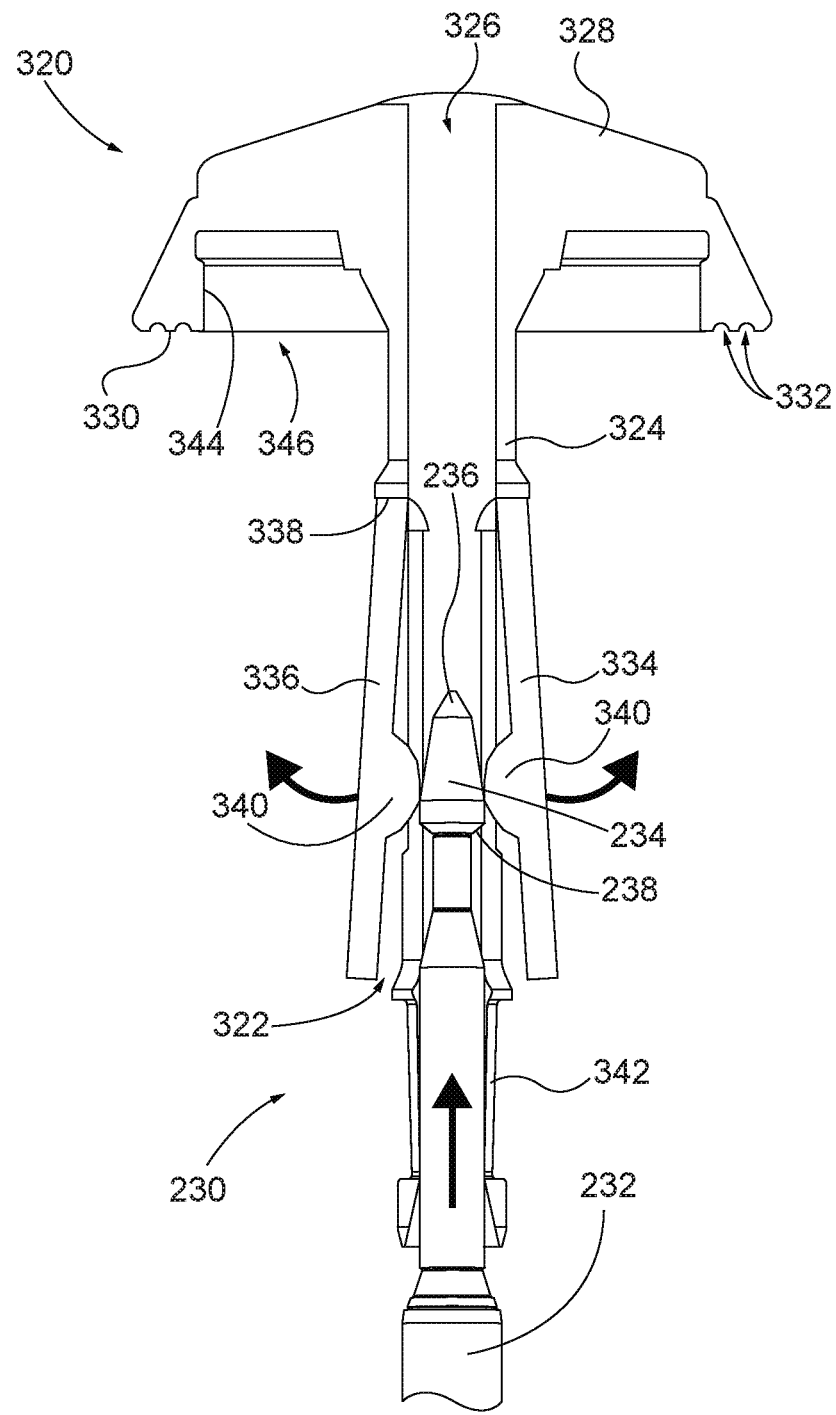
FIG. 15B depicts a cross-sectional view of the trocar of FIG. 15A partially inserted within the anvil of FIG. 12, taken along line 14-14 of FIG. 12.
Figure 15C:
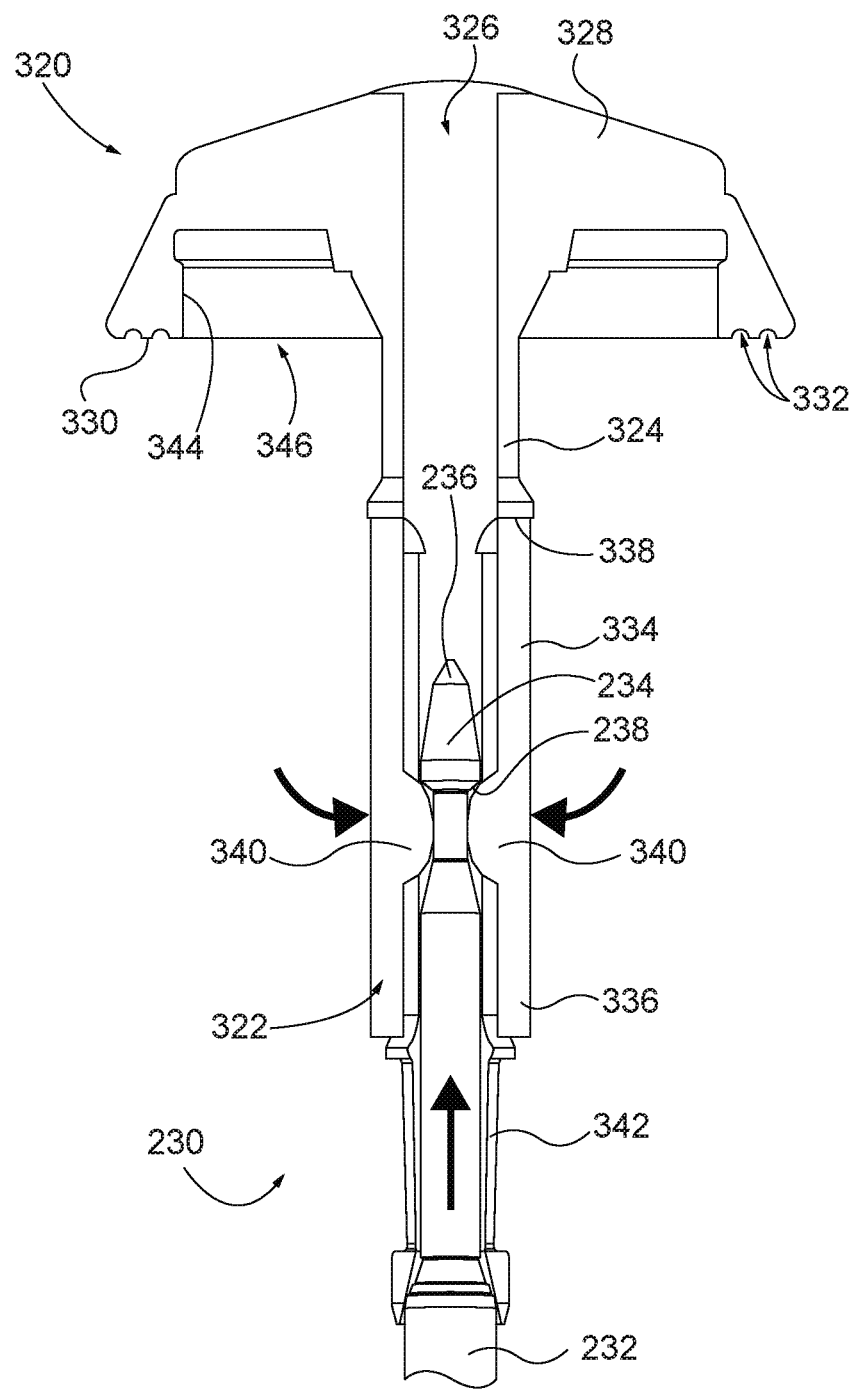
FIG. 15C depicts a cross-sectional view of the trocar of FIG. 15A coupled with the anvil of FIG. 12, taken along line 14-14 of FIG. 12.

FIGS. 15A-15C show an exemplary coupling of anvil (320) and trocar (230). FIG. 15A shows head (234) of trocar (230) placed proximally relative to shank (324) of anvil (320) such that trocar (230) is aligned with bore (326). FIG. 15B shows head (234) of trocar (230) partially inserted into the portion of bore (326) defined by shank (324) prior to anvil (320) being fully seated on trocar (230). At this point, the portion of head (234) distal to proximal surface (238) cams against shelves (340) such that integral pivoting latch members (330) pivot radially outwardly about living hinges (338) to accommodate further insertion of trocar (230) within bore (346).

FIG. 15C shows anvil (320) fully seated on trocar (230) such that proximal surface (338) of trocar (230) and shelves (340) mate against each other. After head (234) of trocar (230) is inserted past shelves (340), head (234) no longer cams against shelves (340) and the resilient nature of pivoting latch members (334) urges proximally extending arms (336) to pivot inwardly toward lateral openings (322)

such that shelves (340) mate against proximally surface (238). In other words, anvil (320) and trocar (230) couple with each other via a snap fitting between pivoting latch members (334) and head (234) of trocar (230). Again, because integral pivoting latch members (334) are formed from material originally forming shank (324) rather than if latch members (334) were separate pieces, potential tolerance stacks associated with latch members (334) relative to shank (324) and head (238) may be reduced or eliminated. This reduction or elimination of tolerance stacking may allow indicator (104) to provide a more accurate display of gap distance d during exemplary use.

Figure 16:
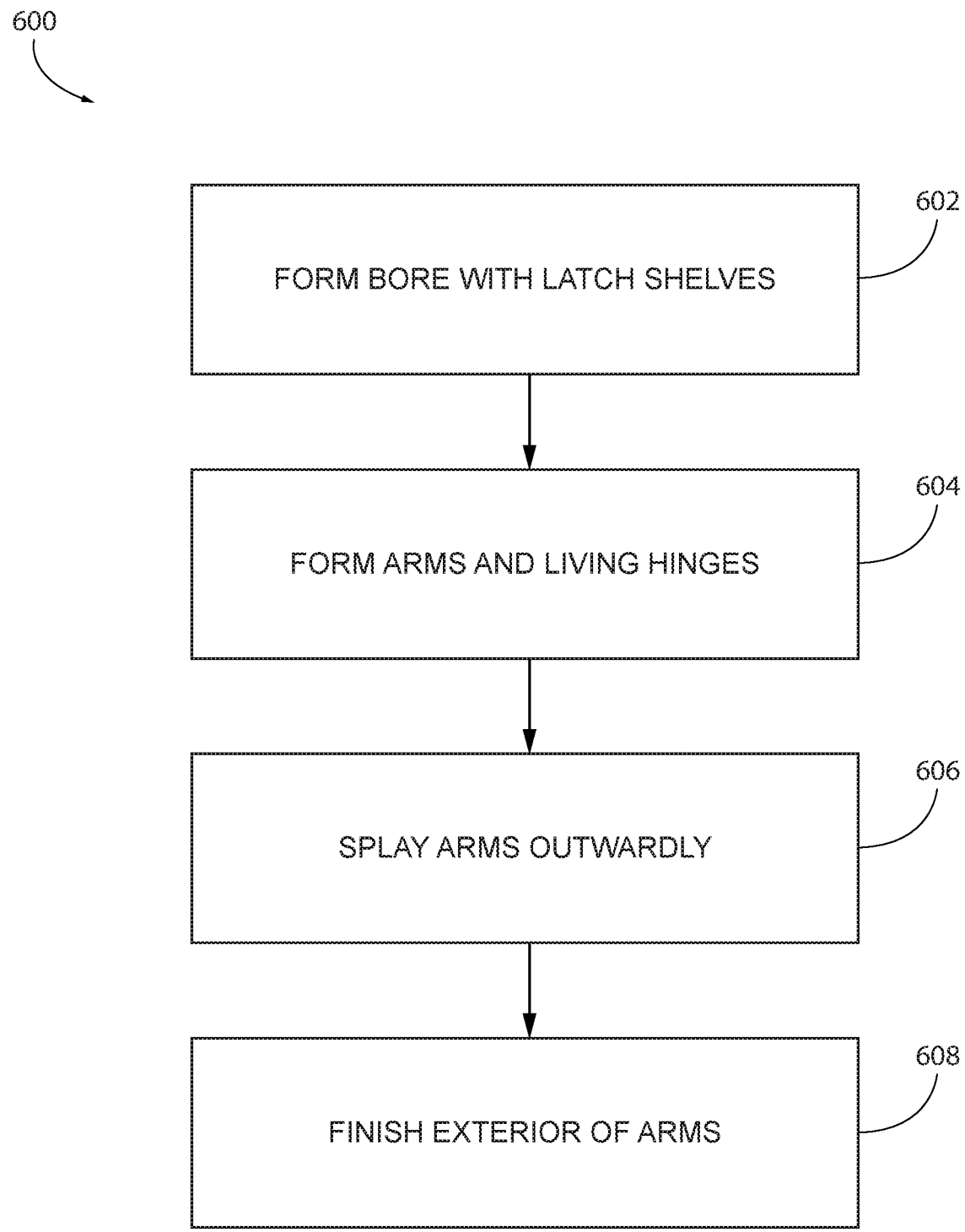
FIG. 16 depicts a flow chart of an exemplary method of manufacturing at least one unitary latch of the anvil of FIG. 12.

FIG. 16 shows an exemplary manufacturing process (600) for creating integral pivoting latch members (334) from material originally forming shank (324). First, anvil (320) may start off as a single piece of material (e.g., steel or some other metal) such that the general exterior shape of anvil head (328) and shank (324) are formed. It should be understood that various features of anvil (320) not specifically mentioned in this manufacturing process (600) may be formed at any suitable time before or after manufacturing process (600). As previously noted, the general exterior shape of anvil head (328) and shank (324) may be formed through machining or any other suitable manufacturing process that would be apparent to one having ordinary skill in the art in view of the teachings herein.

Initially, bore (326) is not yet defined. Therefore, a manufacturer may place the initial anvil (320) on a suitable fixture and drill (block 602) proximally through the distal surface of anvil head (328) and distally through the proximal surface of shank (324) (i.e. shaft) in order to define bore (326). Drilling from each side of anvil (320) may stop at a predetermined location within shank (324) such that latch shelves (340) are initially formed. Once bore (326) is defined and latch shelves (340) are formed, a manufacturer may then laser cut (block 604) the exterior of shank (324) to form proximally extending arms (336) of latch members (334) such that latch members (334) are connected to shank (324) via living hinges (328). With proximally extending arms (336) formed, lateral openings (322) are also formed. While the current example uses laser cutting, any other suitable cutting process may be used as would be apparent to one having ordinary skill in the art in view of the teachings herein. For example, an electrical discharge machining (EDM) process may be used.

With proximally extending arms (336) initially formed, a manufacturer may then insert a suitable mandrel into bore (326) directly adjacent to arms (336) and then splay (block 606) arms (336) radially outwardly relative to lateral openings (322). This splaying process (block 606) may help ensure proximally extending arms (336) are entirely separated from the rest of shank (324) defining lateral openings. After arms (336) have been sufficiently separated, the manufacturer may then perform finishing processes (block 608) on the exterior of splayed arms (336). This finishing process (block 608) may include de-burring and/or other operations to smooth out surfaces and edges as needed; and or other finishing operations as will be apparent to those of ordinary skill in the art in view of the teachings herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a body; (b) an end effector located distally relative to the body, wherein the end effector comprises a staple driver and a plurality of staples, wherein the staple driver is operable to actuate relative to the body between an unfired position and a fired position to drive the plurality of staples distally; (c) a trocar configured to actuate relative to the end effector; and (d) an anvil configured to selectively couple with the trocar such that the trocar is operable to move the anvil into a staple forming position relative to the end effector, wherein the anvil comprises: (i) an anvil head comprising an annular surface defining a plurality of staple forming pockets, wherein the plurality of staple forming pockets are configured to deform the plurality of staples when the anvil is in the staple forming position, (ii) a shank extending proximally from the annular stapling head, wherein the shank and the anvil head cooperatively define a bore dimensioned to receive a portion of the trocar, wherein the shank defines a lateral opening, and (iii) a latch member pivotally coupled with the shank via a living hinge, wherein the latch member comprises a latch shelf configured to selectively couple the anvil with trocar when the trocar is inserted into the bore.

Example 2

The apparatus of Example 1, wherein the latch member further comprises a proximally extending arm coupling the latch shelf with the living hinge, wherein the proximally extending arm is located within the lateral opening defined by the shank.

Example 3

The apparatus of Example 2, wherein the proximally extending arm is biased radially inwardly toward the bore.

Example 4

The apparatus of Example 3, wherein the living hinge is located at a distal-most position along the lateral opening.

Example 5

The apparatus of any one or more of Examples 1 through 4, wherein the shank, the latch member, and the anvil together define a homogenous continuum of material.

Example 6

The apparatus of any one or more of Examples 1 through 5, wherein the living hinge is located proximal relative to the anvil head.

Example 7

The apparatus of any one or more of Examples 1 through 6, wherein the latch shelf is positioned within the bore.

Example 8

The apparatus of any one or more of Examples 1 through 7, wherein the shank of the anvil further comprises a necked-down portion configured for grasping the shank.

Example 9

A method of manufacturing an integral latch member for an anvil configured for use with a circular stapling instrument, the method comprising: (a) securing the anvil on a fixture; (b) drilling through a distal surface in a proximal direction to a first predetermined position to define a first portion of a bore; (c) drilling through a proximal surface in a distal direction to a second predetermined position define a second portion of the bore, wherein drilling to the first predetermined position and the second predetermined position forms a latch shelf extending radially inwardly from an interior surface defining the bore; and (d) cutting an exterior surface of the anvil around the latch shelf in order to form a pivoting arm that is connected to the latch shelf, wherein the pivoting arm is pivotally connected to the rest of the anvil via a living hinge.

Example 10

The method of Example 9, wherein cutting the exterior surface of the anvil comprises laser cutting.

Example 11

The method of any one or more of Examples 9 through 10, further comprising inserting a mandrel into the bore and adjacent to the formed pivoting arm and thereby splaying the pivoting arm and the latch shelf radially outwardly.

Example 12

The method of Example 11, further comprising performing a finishing process on the exterior of the splayed arm.

Example 13

The method of any one or more of Examples 9 through 12, wherein cutting the exterior surface of the anvil to form a pivoting arm also defines a lateral opening from the exterior of anvil toward the bore.

Example 14

The method of any one or more of Examples 9 through 13, wherein an anvil head defines the distal surface and a proximally extending shaft defines the proximal surface.

Example 15

The method of Example 14, wherein the anvil head and the proximally extending shaft together define a homogenous continuum of material.

Example 16

An anvil configured for use with a circular stapling instrument, the anvil comprising: (a) a head comprising and an annular surface defining an annular array of staple forming pockets; (b) a shank extending proximally from the head, wherein the shank and the head cooperatively define a bore, wherein the shank defines a lateral opening; and (c) a latch member, wherein the latch member comprises: (i) a proximally extending arm located within the lateral opening, wherein the proximally extending arm is pivotally coupled with the shank via a living hinge, and (ii) a latch shelf extending inwardly from the proximally extending arm into the bore.

Example 17

The anvil of Example 16, wherein the shank and the latch member together define a homogenous continuum of material.

Example 18

The anvil of Example 17, wherein the shank and the head together define a homogenous continuum of material.

Example 19

The anvil of any one or more of Examples 16 through 18, wherein the bore extends through a distal end of the head and a proximal end of the shank.

Example 20

The anvil of any one or more of Examples 16 through 19, wherein the latch member is resiliently biased radially inwardly toward a longitudinal axis defined by the shank.

IV. Miscellaneous

Any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. patent application Ser. No. 13/693,430, entitled "Trans-Oral Circular Anvil Introduction System with Dilation Feature," filed Dec. 4, 2012, issued as U.S. Pat. No. 9,572,573 on Feb. 21, 2017, the disclosure of which is incorporated by reference herein; U.S. patent application Ser. No. 13/688,951, entitled "Surgical Staple with Integral Pledget for Tip Deflection," filed Nov. 29, 2012, issued as U.S. Pat. No. 9,289,207 on Mar. 22, 2016, the disclosure of which is incorporated by reference herein; U.S. patent application Ser. No. 13/706,827, entitled "Surgical Stapler with Varying Staple Widths along Different Circumferences," filed Dec. 6, 2012, now abandoned, the disclosure of which is incorporated by reference herein; U.S. patent application Ser. No. 13/688,992, entitled "Pivoting Anvil for Surgical Circular Stapler," filed Nov. 29, 2012, issued as U.S. Pat. No. 9,498,222 on Nov. 22, 2016, the disclosure of which is incorporated by reference herein; U.S. patent application Ser. No. 13/693,455, entitled "Circular Anvil Introduction System with Alignment Feature," filed Dec. 4, 2012, issued as U.S. Pat. No. 9,724,100 on Aug. 8, 2017, the disclosure of which is incorporated by reference herein; U.S. patent application Ser. No. 13/716,313, entitled "Circular Stapler with Selectable Motorized and Manual Control, Including a Control Ring," filed Dec. 17, 2012, issued as U.S. Pat. No. 9,532,783 on Jan. 3, 2017, the disclosure of which is incorporated by reference herein; U.S. patent application Ser. No. 13/716,318, entitled "Motor Driven Rotary Input Circular Stapler with Modular End Effector," filed Dec. 17, 2012, issued as U.S. Pat. No. 9,597,081 on Mar. 21, 2017, the disclosure of which is incorporated by reference herein; and/or U.S. patent application Ser. No. 13/716,323, entitled "Motor Driven Rotary Input Circular Stapler with Lockable Flexible Shaft," filed Dec. 17, 2012, issued as U.S. Pat. No. 9,463,022 on Oct. 11, 2016, the disclosure of which is incorporated by reference herein. Various suitable ways in which such teachings may be combined will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a body;
   (b) an end effector located distally relative to the body, wherein the end effector comprises a staple driver and a plurality of staples, wherein the staple driver is operable to actuate relative to the body between an unfired position and a fired position to drive the plurality of staples distally;
   (c) a trocar configured to actuate relative to the end effector; and
   (d) an anvil configured to selectively couple with the trocar such that the trocar is operable to move the anvil into a staple forming position relative to the end effector, wherein the anvil comprises:
      (i) an anvil head comprising an annular surface defining a plurality of staple forming pockets, wherein the plurality of staple forming pockets are configured to deform the plurality of staples when the anvil is in the staple forming position,
      (ii) a shank extending proximally relative to the annular surface, wherein the shank and the anvil head cooperatively define a bore dimensioned to receive a portion of the trocar, wherein the shank defines a lateral opening such that the shank encloses the lateral opening, and
      (iii) a latch member pivotally coupled with the shank via a living hinge located directly adjacent to a portion of the shank defining the lateral opening, wherein the latch member comprises a latch shelf configured to selectively couple the anvil with trocar when the trocar is inserted into the bore.

2. The apparatus of claim 1, wherein the latch member further comprises a proximally extending arm coupling the latch shelf with the living hinge, wherein the proximally extending arm is located within the lateral opening defined by the shank.

3. The apparatus of claim 2, wherein the proximally extending arm is biased radially inwardly toward the bore.

4. The apparatus of claim 3, wherein the living hinge is located at a distal-most position along the lateral opening.

5. The apparatus of claim 1, wherein the shank, the latch member, and the anvil together define a homogenous continuum of material.

6. The apparatus of claim 1, wherein the living hinge is located proximal relative to the anvil head.

7. The apparatus of claim 1, wherein the latch shelf is positioned within the bore.

8. The apparatus of claim 1, wherein the shank of the anvil further comprises a necked-down portion configured for grasping the shank.

9. A method of manufacturing an integral latch member for an anvil configured for use with a circular stapling instrument, the method comprising:
   (a) securing the anvil on a fixture;
   (b) drilling through a distal surface in a proximal direction to a first predetermined position to define a first portion of a bore;
   (c) drilling through a proximal surface in a distal direction to a second predetermined position define a second portion of the bore, wherein drilling to the first predetermined position and the second predetermined position forms a latch shelf extending radially inwardly from an interior surface defining the bore; and
   (d) cutting an exterior surface of the anvil around the latch shelf in order to form a pivoting arm that is connected to the latch shelf, wherein the pivoting arm is pivotally connected to the rest of the anvil via a living hinge.

10. The method of claim 9, wherein cutting the exterior surface of the anvil comprises laser cutting.

11. The method of claim 9, further comprising inserting a mandrel into the bore and adjacent to the formed pivoting arm and thereby splaying the pivoting arm and the latch shelf radially outwardly.

12. The method of claim 11, further comprising performing a finishing process on the exterior of the splayed arm.

13. The method of claim 9, wherein cutting the exterior surface of the anvil to form a pivoting arm also defines a lateral opening from the exterior of anvil toward the bore.

14. The method of claim 9, wherein an anvil head defines the distal surface and a proximally extending shaft defines the proximal surface.

15. The method of claim 14, wherein the anvil head and the proximally extending shaft together define a homogenous continuum of material.

16. An anvil configured for use with a circular stapling instrument, the anvil comprising:
   (a) a head comprising and an annular surface defining an annular array of staple forming pockets;
   (b) a shank extending proximally from the head, wherein the shank and the head cooperatively define a bore, wherein the shank defines a lateral opening, wherein the shank encloses the lateral opening; and
   (c) a latch member, wherein the latch member comprises:
      (i) a proximally extending arm located within the lateral opening, wherein the proximally extending arm is pivotally coupled with the shank via a living hinge located directly adjacent to a portion of the shank defining the lateral opening, and
      (ii) a latch shelf extending inwardly from the proximally extending arm into the bore.

17. The anvil of claim 16, wherein the shank and the latch member together define a homogenous continuum of material.

18. The anvil of claim 17, wherein the shank and the head together define a homogenous continuum of material.

19. The anvil of claim 16, wherein the bore extends through a distal end of the head and a proximal end of the shank.

20. The anvil of claim 16, wherein the latch member is resiliently biased radially inwardly toward a longitudinal axis defined by the shank.

* * * * *